(12) United States Patent
Allgeier et al.

(10) Patent No.: US 6,656,957 B1
(45) Date of Patent: Dec. 2, 2003

(54) PYRIDINE DERIVATIVES

(75) Inventors: Hans Allgeier, Lörrach (DE); Yves Auberson, Allschwil (CH); Michel Biollaz, Binningen (CH); Nicholas David Cosford, San Diego, CA (US); Fabrizio Gasparini, Lausen (CH); Roland Heckendorn, Arlesheim (CH); Edwin Carl Johnson, San Diego, CA (US); Rainer Kuhn, Lörrach (DE); Mark Andrew Varney, San Diego, CA (US); Gönül Veliçelebi, San Diego, CA (US)

(73) Assignees: Novartis AG, Basel (CH); Sibia Neurosciences Inc., La Jolla, CA (US)

( * ) Notice: Subject to any disclaimer, the term of this patent is extended or adjusted under 35 U.S.C. 154(b) by 0 days.

(21) Appl. No.: 09/722,803

(22) Filed: Nov. 27, 2000

Related U.S. Application Data

(63) Continuation of application No. 09/462,511, filed as application No. PCT/EP98/04266 on Jul. 9, 1998, now abandoned.

(51) Int. Cl.$^7$ .................. C07D 401/12; A61K 31/44
(52) U.S. Cl. ................ 514/332; 514/252.18; 514/256; 514/277; 514/312; 514/338; 514/342; 514/352; 544/333; 544/360; 546/153; 546/280.4; 546/282.4; 546/233.7; 546/346
(58) Field of Search .................... 546/255, 153, 546/280.4, 282.4, 233.7, 346; 514/332, 252.18, 256, 277, 312, 338, 342, 352; 544/333, 360

(56) References Cited

U.S. PATENT DOCUMENTS

| 4,006,240 A | 2/1977 | Ho et al. ............. 514/277 |
| 5,013,744 A | 5/1991 | Chandraratna ......... 514/345 |

FOREIGN PATENT DOCUMENTS

| EP | 181 568 A2 | 5/1986 |
| EP | 334 119 A | 9/1989 |
| WO | WO 92/23357 | 11/1993 |
| WO | WO 97 05109 A | 2/1997 |
| WO | WO 97 19049 A | 5/1997 |

OTHER PUBLICATIONS

Dowell, R.I. et al., European Journal of Medicinal Chemistry, vol. 28, No. 6, pp. 513–516 (1993).
Lazer, E.S. et al., Journal of Medicinal Chemistry, vol. 33, No. 7, pp. 1892–1898 (1990).
Bahner, C.T. et al., Arzneim, Forsch./Drug Res., vol. 31, No. 3, pp. 404–406 (1981).
Honma, Y. et al., Journal of Medicinal Chemistry, vol. 27, No. 2, pp. 125–128 (1984).
Mori, M. et al., Agricultural and Biological Chemistry, vol. 46, No. 1, pp. 309–311 (1982).
Jerchel, D. et al., Justus Liebigs Ann.Chem., vol. 613, pp. 171–177 (1958).
Chemical Abstracts, vol. 53, 5263g (1957).
Sadao, Arai et al., Journal of Heterocyclic Chemistry, vol. 29, pp. 215–220 (1992).
Shaw, B.D. et al., Journal of the Chemical Society, pp. 79–83 (1932).
Derwent Abstract 82777 D/45, J5 6123–903, Sep. 29, 1981.
Derwent Abstract 00693 E/01, J5 6154–401, Nov. 30, 1981.

Primary Examiner—Zinna Northington Davis
(74) Attorney, Agent, or Firm—Joseph J. Borovian

(57) ABSTRACT

A compound of formula I

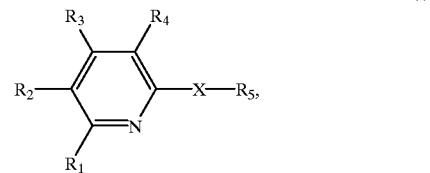

wherein

X represents an optionally halo-substituted $(C_{2-4})$ alkynylene group bonded via vicinal unsaturated carbon atoms.

8 Claims, No Drawings

PYRIDINE DERIVATIVES

This is a continuation of U.S. application Ser. No. 09/462,511, having a 371 date of Feb. 24, 2000, now abandoned, which application is a 371 of International Application No. PCT/EP98/04266, filed Jul. 9, 1998.

The invention relates to the use of 2-arylalkenyl-, 2-heteroarylalkenyl-, 2-arylalkynyl-, 2-heteroarylalkynyl-, 2-arylazo- and 2-heteroarylazo-pyridines for modulating the activity of mGluRs and for treating mGluR5 mediated diseases, to pharmaceutical compositions for use in such therapy, as well as to novel 2-arylalkenyl-, 2-heteroarylalkenyl-, 2-arylalkynyl-, 2-heteroarylalkynyl-, 2-arylazo- and 2-heteroarylazo-pyridines.

It has been found that 2-arylalkenyl-, 2-heteroarylalkenyl-, 2-arylalkynyl-, 2-heteroarylalkynyl-, 2-arylazo- and 2-heteroarylazo-pyridines including the pharmaceutically acceptable salts (hereinafter agents of the invention) are useful as modulators of mGluRs. Modulation of mGluRs can be demonstrated in a variety of ways, inter alia, in binding assays and functional assays such as second messenger assays or measurement of changes in intracellular calcium concentrations. For example, measurement of the inositol phosphate turnover in recombinant cell lines expressing hmGluR5a showed, for selected agents of the invention, $IC_{50}$ values of about 1 nM to about 50 μM.

In particular, the agents of the invention have valuable pharmacological properties. For example, they exhibit a marked and selective modulating, especially antagonistic, action at human metabotropic glutamate receptors (mGluRs). This can be determined in vitro for example at recombinant human metabotropic glutamate receptors, especially PLC-coupled subtypes thereof such as mGluR5, using different procedures like, for example, measurement of the inhibition of the agonist induced elevation of intracellular $Ca^{2+}$ concentration in accordance with L. P. Daggett et al. Neuropharm. Vol. 34, pages 871–886 (1995), P. J. Flor et al., J. Neurochem. Vol. 67, pages 58–63 (1996) or by determination to what extent the agonist induced elevation of the inositol phosphate turnover is inhibited as described by T. Knoepfel et al. Eur. J. Pharmacol. Vol. 288, pages 389–392 (1994), L. P. Daggett et al., Neuropharm. Vol. 67, pages 58–63 (1996) references cited therein. Isolation and expression of human mGluR subtypes are described in U.S. Pat. No. 5,521,297. Selected agents of the invention showed $IC_{50}$ values for the inhibition of the quisqualate-induced inositol phosphate turnover, measured in recombinant cells expressing hmGluR5a of about 1 nM to about 50 μM.

Accordingly the invention relates to agents of the invention for use in the treatment of disorders associated with irregularities of the glutamatergic signal transmission, and of nervous system disorders mediated lull or in part by mGluR5.

Disorders associated with irregularities of the glutamatergic signal transmission are for example epilepsy, cerebral ischemias, especially acute ischemias, ischemic diseases of the eye, muscle spasms such as local or general spasticity and, in particular, convulsions or pain.

Nervous system disorders mediated full or in part by mGluR5 are for example acute, traumatic and chronic degenerative processes of the nervous system, such as Parkinson's disease, senile dementia, Alzheimer's disease, Huntington's chorea, amyotrophic lateral sclerosis and multiple sclerosis, psychiatric diseases such as schizophrenia and anxiety, depression and pain.

The invention also relates to the use of agents of the invention, in the treatment of disorders associated with irregularities of the glutamatergic signal transmission, and of nervous system disorders mediated full or in part by Group I mGluRs.

Furthermore the invention relates to the use of agents of the invention for the manufacture of a pharmaceutical composition designed for the treatment of disorders associated with irregularities of the glutamatergic signal transmission, and of nervous system disorders mediated full or in part by Group I mGluRs.

In a further aspect the invention relates to a method of treating disorders mediated full or in part by group I mGluRs (preferentially mGluR5) which method comprises administering to a warm-blooded organism in need of such treatment a therapeutically effective amount of an agent of the invention.

In still a further aspect, the invention relates to novel 2-arylalkenyl-, 2-heteroarylalkenyl-, 2-arylalkynyl-, 2-heteroarylalkynyl-, 2-arylazo- and 2-heteroarylazo-pyridines and their salts, and to a process for preparing them.

Moreover the invention relates to a pharmaceutical composition comprising as pharmaceutical active ingredient, together with customary pharmaceutical excipients, a novel 2-arylalkenyl-, 2-heteroarylalkenyl-, 2-arylalkynyl-, 2-heteroarylalkynyl-, 2-arylazo- or 2-heteroarylazo-pyridine or a pharmaceutically acceptable salt thereof.

Agents of the invention are for example compounds of formula I

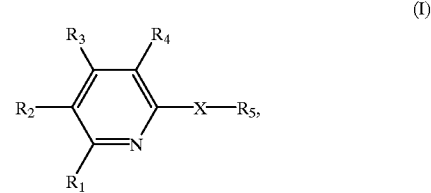

wherein $R_1$ denotes hydrogen, lower alkyl, hydroxy-lower alkyl lower alkyl-amino, piperidino, carboxy, esterified carboxy, amidated carboxy, unsubstituted or lower alkyl-, lower alkoxy-, halo- and/or trifluoromethyl-substituted N-lower-alkyl-N-phenylcarbamoyl, lower alkoxy, halo-lower alkyl or halo-lower alkoxy, $R_2$ denotes hydrogen, lower alkyl, carboxy, esterified carboxy, amidated carboxy, hydroxy-lower alkyl, hydroxy, lower alkoxy or lower alkanoyloxy, 4-(4-fluoro-benzoyl)-piperidin-1-yl-carboxy, 4-t.-butyloxycarbonyl-piperazin-1-yl-carboxy, 4-(4-azido-2-hydroxybenzoyl)-piperazin-1-yl-carboxy or 4-(4-azido-2-hydroxy-3-iodo-benzoyl)-piperazin-1-yl-carboxy, $R_3$ represents hydrogen, lower alkyl, carboxy, lower alkoxy-carbonyl, lower alkyl-carbamoyl, hydroxy-lower alkyl, di- lower alkyl- aminomethyl, morpholinocarbonyl or 4-(4-fluoro-benzoyl)-piperidin-1-yl-carboxy, $R_4$ represents hydrogen, lower alkyl, hydroxy, hydroxy-lower alkyl, amino-lower alkyl, lower alkylamino-lower alkyl, di-lower alkylamino-lower alkyl, unsubstituted or hydroxy-substituted lower alkyleneamino-lower alkyl, lower alkoxy, lower alkanoyloxy, amino-lower alkoxy, lower alkylamino-lower alkoxy, di-lower alkylamino-lower alkoxy, phthalimido-lower alkoxy, unsubstituted or hydroxy- or 2-oxo-imidazolidin-1-yl-substituted lower alkyleneamino-lower alkoxy, carboxy, esterified or amidated carboxy, carboxy-lower-alkoxy or esterified carboxy-lower-alkoxy, X represents an optionally halo-substituted lower alkenylene or alkynylene group bonded via vicinal unsaturated carbon atoms or an azo (—N=N—) group, and $R_5$ denotes an aromatic or heteroaromatic group which is unsubstituted or substituted by one or more substituents selected from lower alkyl, halo, halo-lower alkyl, halo-lower alkoxy, lower alkenyl, lower alkynyl, unsubstituted or lower alkyl-, lower alkoxy-, halo- and/or trifluoromethyl-substituted phenyl, unsubstituted or lower alkyl-, lower alkoxy-, halo- and/or trifluoromethyl-substituted phenyl-lower alkynyl, hydroxy, hydroxy-lower alkyl, lower alkanoyloxy-lower alkyl, lower alkoxy, lower alkenyloxy, lower alkylenedioxy, lower alkanoyloxy, amino-, lower alkylamino-, lower alkanoylamino- or N-lower alkyl-N-lower alkanoylamino-lower alkoxy, unsubstituted or lower alkyl- lower alkoxy-, halo- and/or trifluoromethyl-substituted phenoxy, unsubstituted or lower alkyl- lower alkoxy-, halo- and/or trifluoromethyl-substituted phenyl-lower alkoxy, acyl, carboxy, esterified carboxy, amidated carboxy, cyano, carboxy-lower alkylamino, esterified carboxy-lower alkylamino, amidated carboxy-lower alkylamino, phosphono-lower alkylamino, esterified phosphono-lower alkylamino, nitro, amino, lower alkylamino, di-lower alkylamino, acylamino, N-acyl-N-lower alkylamino, phenylamino, phenyl-lower alkylamino, cycloalkyl-lower alkylamino or heteroaryl-lower alkylamino each of which may be unsubstituted or lower alkyl- lower alkoxy-, halo- and/or trifluoromethyl-substituted, customary photoaffinity ligands and customary radioactive markers, inclusive of their N-oxides and their pharmaceutically acceptable salts.

Compounds of formula I having basic groups may form acid addition salts, and compounds of the formula I having acidic groups may form salts with bases. Compounds of formula I having basic groups and in addition having at least one acidic group, may also form internal salts.

Also included are both total and partial salts, that is to say salts with 1, 2 or 3, preferably 2, equivalents of base per mole of acid of formula I, or salts with 1, 2 or 3 equivalents, preferably 1 equivalent, of acid per mole of base of formula I.

For the purposes of isolation or purification it is also possible to use pharmaceutically unacceptable salts. Only the pharmaceutically acceptable, non-toxic salts are used therapeutically and they are therefore preferred.

Halo in the present description denotes fluorine, chlorine, bromine or iodine.

When X represents an alkenylene group, configuration trans is preferred.

Preferred compounds of formula I are those wherein

X represents an optionally halo-substituted $(C_{2-4})$ alkenylene or alkynylene group bonded via vicinal unsaturated carbon atoms, $R_1$ is hydrogen, $(C_{1-4})$ alkyl, $(C_{1-4})$alkoxy, hydroxy$(C_{1-4})$ alkyl, cyano, ethynyl, carboxy, $(C_{1-4})$alkoxycarbonyl, di$(C_{1-4})$alkylamino, $(C_{1-6})$alkylaminocarbonyl, or trifluoromethylphenylaminocarbonyl, $R_2$ is hydrogen, hydroxy, $(C_{1-4})$ alkyl, hydroxy $(C_{1-4})$ alkyl, $(C_{1-4})$ alkoxy, carboxy, $(C_{2-5})$alkanoyloxy, $(C_{1-4})$ alkoxycarbonyl, di$(C_{1-4})$alkylamino$(C_{1-4})$alkanoyl, di$(C_{1-4})$alkylaminomethyl, 4-(4-fluoro-benzoyl)-piperidin-1-yl-carboxy, 4-t.-butyloxycarbonyl-piperazin-1-yl-carboxy, 4-(4-azido-2-hydroxybenzoyl)-piperazin-1-yl-carboxy or 4-(4-azido-2-hydroxy-3-iodo-benzoyl)-piperazin-1-yl-carboxy, $R_3$ is hydrogen, $(C_{1-4})$ alkyl, carboxy, $(C_{1-4})$ alkoxycarbonyl, $(C_{1-4})$alkylcarbamoyl, hydroxy$(C_{1-4})$ alkyl, di$(C_{1-4})$alkylaminomethyl, morpholinocarbonyl or 4-(4-fluoro-benzoyl)-piperidin-1-yl-carboxy, $R_4$ is hydrogen, hydroxy, $(C_{1-4})$alkoxy, carboxy, $(C_{2-5})$ alkanoyloxy, $(C_{1-4})$alkoxycarbonyl, amino$(C_{1-4})$ alkoxy, di$(C_{1-4})$alkylamino$(C_{1-4})$alkoxy, di$(C_{1-4})$ alkylamino$(C_{1-4})$alkyl, carboxy $(C_{1-4})$alkylcarbonyl, $(C_{1-4})$alkoxycarbonyl$(C_{1-4})$alkoxy, hydroxy$(C_{1-4})$ alkyl, di$(C_{1-4})$alkylamino$(C_{1-4})$alkoxy, m-hydroxy-p-azidophenylcarbonylamino$(C_{1-4})$alkoxy, or and $R_5$ is a group of formula

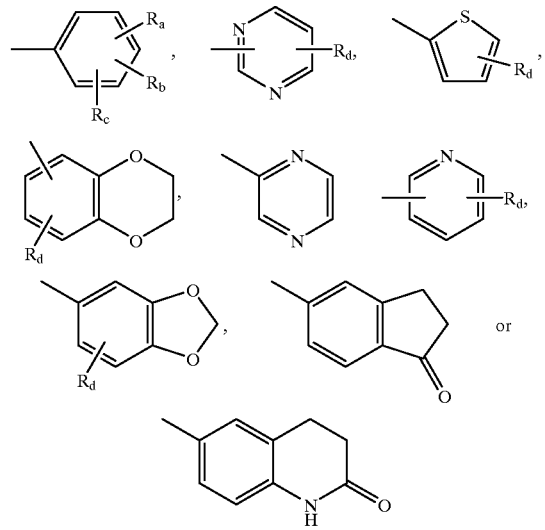

wherein $R_a$ and $R_b$ independently are hydrogen, hydroxy, halogen, nitro, cyano, carboxy, $(C_{1-4})$alkyl, $(C_{1-4})$ alkoxy, hydroxy$(C_{1-4})$alkyl, $(C_{1-4})$alkoxycarbonyl, $(C_{2-7})$alkanoyl, $(C_{2-5})$alkanoyloxy, $(C_{2-5})$ alkanoyloxy $(C_{1-4})$alkyl, trifluoromethyl, trifluoromnethoxy, trimethylsilylethynyl, $(C_{2-5})$ alkynyl, amino, azido, amino $(C_{1-4})$alkoxy, $(C_{2-5})$ alkanoylamino $(C_{1-4})$alkoxy, $(C_{1-4})$alkylamino $(C_{1-4})$alkoxy, di$(C_{1-4})$alkylamino $(C_{1-4})$alkoxy, $(C_{1-4})$ alkylamino, di$(C_{1-4})$alkylamino, monohalobenzylamino, thienylmethylamino, thienylcarbonylamino, trifluoromethylphenylaminocarbonyl, tetrazolyl, $(C_{2-5})$alkanoylamino, benzylcarbonylamino, $(C_{1-4})$ alkylaminocarbonylamino, $(C_{1-4})$alkoxycarbonyl-aminocarbonylamino or $(C_{1-4})$alkylsulfonyl, $R_c$ is hydrogen, fluorine, chlorine, bromine, hydroxy, $(C_{1-4})$alkyl, $(C_{2-5})$alkanoyloxy, $(C_{1-4})$alkoxy or cyano, and $R_d$ is hydrogen, halogen or $(C_{1-4})$alkyl.

More preferred compounds of formula I are those wherein X is as defined above and $R_1$ is hydrogen, $(C_{1-4})$ alkyl, $(C_{1-4})$alkoxy, cyano, ethynyl or di$(C_{1-4})$alkylamino, $R_2$ is hydrogen, hydroxy, carboxy, $(C_{1-4})$ alkoxycarbonyl, di$(C_{1-4})$alkylaminomethyl, 4-(4-fluoro-benzoyl)-piperidin-1-yl-carboxy, 4-t.-butyloxycarbonylpiperazin-1-yl-carboxy, 4-(4-azido-2-hydroxybenzoyl)-piperazin-1-yl-carboxy or 4-(4-azido-2-hydroxy-3-iodo-benzoyl)-piperazin-1-yl-carboxy, $R_3$ is as defined above, $R_4$ is hydrogen, hydroxy, carboxy, $(C_{2-5})$alkanoyloxy, $(C_{1-4})$alkoxycarbonyl, amino/$(C_{1-4})$alkoxy, di$(C_{1-4})$alkylamino$(C_{1-4})$alkoxy, di$(C_{1-4})$alkylamino$(C_{1-4})$alkyl or hydroxy$(C_{1-4})$alkyl, and $R_5$ is a group of formula

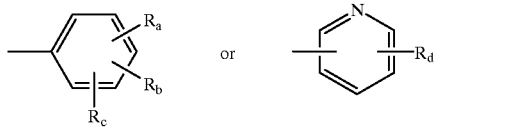

wherein $R_a$ and $R_b$ independently are hydrogen, halogen, nitro, cyano, $(C_{1-4})$alkyl, $(C_{1-4})$alkoxy, trifluoromethyl, trifluoromethoxy or $(C_{2-5})$alkynyl, and $R_c$ and $R_d$ are as defined above.

The agents of the invention include, for example, the compounds described in the examples hereinafter.

The usefulness of the agents of the invention in the treatment of the above-mentioned disorders could be confirmed in a range of standard tests including those indicated below:

At doses of about 10 to 100 mg/kg i.p. or p.o. with pretreatment times of 15 min. to 8 hours, the agents of the invention show anticonvulsive activity in the electroshock induced convulsion model [cf. E. A. Swinyard, J. Pharm. Assoc. Scient. Ed. 38, 201 (1949) and J. Pharmacol. Exptl. Therap. 106, 319 (1952)].

At doses of about 4 to about 40 mg/kg p.o., the agents of the invention show reversal of Freund complete adjuvant (FCA) induced hyperalgesia [cf. J. Donnerer et al., Neuroscience 49, 693–698 (1992) and C. J. Woolf, Neuroscience 62, 327–331 (1994)].

For all the above mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.5 to about 100 mg/kg animal body weight. In larger mammals, for example humans, an indicated daily dosage is in the range from about 5 to 1500 mg, preferably about 10 to about 1000 mg of the compound conveniently administered in divided doses up to 4 times a day or in sustained release form.

Preferred compounds for the above mentioned indications include (3-{2-[2-trans-(3,5-dichlorophenyl)-vinyl]-6-methyl-pyridin-3-yloxy}-propyl)-dimethylamine (A), 2-methyl-6-styryl-pyridine (B), 2-(3-fluoro-phenylethynyl)-6-methyl-pyridine (C) and 2-(4-ethoxy-3-trifluoromethyl-phenylethynyl)-6-methyl-pyridine (D). It has for example been determined that in the above-mentioned electroshock induced convulsion model, compounds A and B show anticonvulsive activity with $ED_{50}$ of 30 and 35 mg/kg i.p. respectively (pretreatment times: 4 hours and 15 min. respectively) and that in the above-mentioned FCA induced hyperalgesia model, compounds C and D show reversal of the hyperalgesia with $ED_{50}$s of 4.2 and 19 mg/kg p.o. respectively (post-treatment time: 3 hours).

As indicated above, the agents of the invention include novel 2-arylalkenyl-, 2-heteroarylalkenyl-, 2-arylalkynyl-, 2-heteroarylalkynyl-, 2-arylazo- and 2-heteroarylazopyridines and their salts, hereinafter referred to as "compounds of the invention".

Compounds of the invention include compounds of formula I as defined above, and their salts, wherein X and $R_1$ to $R_5$ are as defined above, provided that when $R_3$ is hydrogen, a) in compounds of the formula I in which $R_1$, $R_2$ and $R_4$ are hydrogen, $R_5$ is different from phenyl, monohalophenyl, 2,4- and 3,4-dichlorophenyl, 3- and 4-trifluoromethylphenyl, methylphenyl, 3,4- and 2,5-dimethylphenyl, 4-isopropylphenyl, 3,5-di-tert.-butylphenyl, methoxyphenyl, 3,4-dimethoxyphenyl, 2,4,5- and 3,4,5-trimethoxyphenyl, hydroxyphenyl, 3,5-dihydroxyphenyl, 4-hydroxy-3,5-dimethyl-phenyl, 3-hydroxy-4-methoxy- and 4-hydroxy-3-methoxy-phenyl, 4-hydroxy-(3-methyl-5-tert.-butyl-, 2- and 4-acetylaminophenyl, 3,5-diisopropyl- and 3,5-di-tert.-butyl)phenyl, 4-carboxy- and 4-ethoxycarbonylphenyl, 4-cyanophenyl, 3-methoxycarbonylphenyl, 3-carboxy-5-methoxy-phenyl, 2-pyridinyl, 5-chloro-2-pyridinyl and 6-methyl-2-pyridinyl when X denotes ethenylene, or $R_5$ is different from phenyl, 4-methylphenyl, 4-methoxyphenyl, 4-bromophenyl and 2- and 4-chlorophenyl when X denotes 1,2-propylene attached to $R_5$ in 2-position, or $R_5$ is different from phenyl, 2- and 4-chlorophenyl and 3-methoxyphenyl when X denotes 1,2-propylene attached to $R_5$ in 1-position, or $R_5$ is different from 4-methoxyphenyl when X denotes 2,3-but-2-enylene or 1,2-but-1-enylene attached to $R_5$ in 2-position, or $R_5$ is different from 4-methoxyphenyl and 4-isopropyphenyl when X denotes 2,3-pent-2-enylene attached to $R_5$ in 3-position, or $R_5$ is different from phenyl, 4-methylphenyl, methoxyphenyl and 4-hydroxyphenyl when X denotes 3,4-hex-3-enylene;

b) in compounds of the formula I in which $R_1$ is methyl and $R_2$ and $R_4$ are hydrogen, $R_5$ is different from phenyl, 3-methylphenyl, 2-methoxyphenyl, 2-chlorophenyl, 4-cyanophenyl, 2-pyridinyl and 6-methyl-2-pyridinyl when X denotes ethenylene;

c) in compounds of the formula I in which $R_1$ and $R_2$ are hydrogen and $R_4$ is carboxy, $R_5$ is different from phenyl, 3-methylphenyl, 4-methoxyphenyl and 4-bromophenyl when X denotes ethenylene;

d) in compounds of the formula I in which $R_1$ and $R_2$ are hydrogen and $R_4$ is methyl, $R_5$ is different from phenyl, 3-methoxy-, 4-methoxy- and 3,4-dimethoxyphenyl, 2-chloro- and 2,4-dichlorophenyl and 6-methyl-pyrid-2yl when X denotes ethenylene or $R_5$ is different from phenyl when X is 1,2-prop-1-enylene attached to $R_5$ in 2-position;

e) in compounds of the formula I wherein $R_1$ and $R_2$ are hydrogen and $R_4$ is 2-dimethylaminoethoxycarbonyl or 3-dimethylaminopropyloxycarbonyl, $R_5$ is different from 4-methoxy-phenyl when X denotes ethenylene;

f) in compounds of the formula I in which $R_1$ and $R_2$ are hydrogen and $R_4$ is 2-dimethoxyethoxy, $R_5$ is different from phenyl, 4-methylphenyl and 4-methoxycarbonylphenyl when X denotes ethenylene;

g) $R_5$ is different from phenyl when $R_1$ and $R_2$ are hydrogen and $R_4$ is hydroxy or ethoxycarbonyl, or when $R_1$ is methyl, $R_2$ is hydrogen and $R_4$ is methoxy, or $R_1$ is but-1-enyl, $R_2$ is hydrogen and $R_4$ is hydrogen, or $R_1$ is hydrogen and $R_4$ is 2-dimethoxyethoxy, and X is, in each case, ethenylene, and provided that, when $R_3$ is hydrogen and X is ethynylene, a') $R_5$ is different from phenyl, 2- and 4-nitrophenyl, 4-aminophenyl, 4-chlorophenyl, 4-methylphenyl, 4-methoxyphenyl, 4-ethoxycarbonylphenyl, 5-formyl-2-methoxy-phenyl, 5-carboxy-2-methoxy-phenyl and pyridyl when $R_1$, $R_2$ and $R_4$ are hydrogen;

b') in compounds of the formula I in which $R_2$ and $R_4$ are hydrogen, $R_5$ is different from phenyl, 3-methylphenyl. 6-methylpyridin-2-yl and 2-methoxyphenyl when $R_5$ is methyl, $R_5$ is different from 6-bromopyridin-2-yl when $R_1$ is bromo, and $R_5$ is different from 6-hexyloxypyridin-2-yl when $R_1$ denotes hexyloxy;

c') in compounds of the formula I wherein $R_1$ and $R_4$ are hydrogen, $R_5$ is different from phenyl, 4-aminophenyl and 4-propylphenyl when $R_2$ is methyl, $R_5$ is different from phenyl, 4-cyanophenyl and 4-pentylphenyl when $R_2$ is ethyl, $R_5$ is different from 3-cyano-4-ethoxyphenyl and 3-bromo-4-methoxy-phenyl when $R_2$ is butyl, $R_5$ is different from 4-methoxy-phenyl and 4 butyloxyphenyl when $R_2$ is pentyl, $R_5$ is different from 4-ter.-butylphenyl, 3-tert.-butyl-4-hydroxy-phenyl, 4-tert.-butyl-3-hydroxy-phenyl, and 4-hexyloxyphenyl when $R_2$ is carboxy, $R_5$ is different from phenyl when $R_2$ is methoxycarbonyl or methylcarbamoyl, $R_4$ is different from 3-tert.-butylphenyl, 3-tert.-butyl-4-hydroxy-phenyl and 4-(4-methylpentyl)phenyl when $R_2$ is ethoxycarbonyl, and $R_5$ is different from 4-pentyloxyphenyl when $R_2$ is 2-methylbutyloxycarbonyl;

d') in compounds of the formula I wherein $R_1$ and $R_2$ are hydrogen, $R_5$ is different from phenyl when $R_4$ is hydroxy, methyl, ethyl, carboxy, methoxycarbonyl or carbamoyl.

Preferred compounds of the invention are as indicated above for the agents of the invention.

The compounds of the invention can be prepared in analogy to the synthesis of known compounds of formula I.

Thus the compounds of the invention which are of formula I can be prepared for example by a process which comprises a) reacting a compound of the formula II

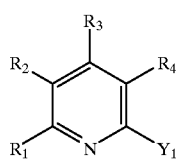

(II)

with a compound of the formula $Y_2$—$R_5$ (III), in which either one of $Y_1$ and $Y_2$ denotes lower alkanoyl and the other one represents lower alkyl or triarylphosphoranylidenemethyl, or one of $Y_1$ and $Y_2$ denotes a reactive esterified hydroxy group and the other one represents a group $Y_3$—X— in which $Y_3$ is hydrogen or a metallic group, and $R_1$, $R_2$, $R_3$, $R_4$ and $R_5$ have the meanings indicated hereinbefore and func tional groups $R_1$, $R_2$, $R_3$ and $R_4$ as well as functional substituents of $R_5$ may be temporarily protected, or b) eliminating H—$Y_4$ from a compound of the formula IV

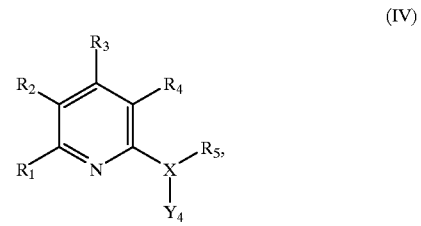

(IV)

in which $Y_4$ denotes an electrofugal group and $R_1$, $R_2$, $R_3$, $R_4$, X and $R_5$ have the meanings indicated hereinbefore and functional groups $R_1$, $R_2$, $R_3$ and $R_4$ as well as functional substituents of $R_5$ may temporarily be protected, removing any temporary protecting groups and, if desired, converting a compound of formula I obtainable by the above-defined processes into a different compound of formula I, resolving a mixture of isomers that may be obtained into the individual isomers and/or converting a compound of formula I having at least one salt-forming group obtainable by the above-defined processes into a salt, or converting a salt obtainable by the above-defined processes into the corresponding free compound or into a different salt.

A lower alkanoyl $Y_2$ or, more preferably, $Y_1$ group is, for example, a $C_1$–$C_3$alkanoyl group, such as formyl, acetyl or propionyl, especially formyl. A lower alkyl group $Y_1$ or, more preferably, $Y_2$ is, for example, a $C_1$–$C_3$alkyl group, such as methyl, ethyl or propyl, especially methyl. Triarylphosphoranylidenemethyl $Y_2$ or, more preferably, $Y_1$ is, for example, triphenylphosphoranylidenemethyl.

When one of $Y_1$ and $Y_2$ denotes a reactive esterified hydroxy group and the other one represents a group of the formula $Y_3$—X— in which $Y_3$ denotes hydrogen, the condensation is preferably performed according to the Heck coupling method, for example, in the presence of copper or of a copper catalyst or of a noble metal/phosphine catalyst, such as Palladium or a PdII salt in the presence of triaryl phosphine, for example, palladium acetate, and of triphenylphosphine, or in the presence of bis-triphenylphosphine-palladium dichloride, preferably in the presence of a tri-lower alkyl amine, for example, trimethylamine, advantageously in the presence of $Cu^{I}$—I, in a polar organic solvent such as N,N-di-lower alkyl-alkanoic acid amide, for example, dimethylformamide, a di-lower alkyl sulfoxide, for example, dimethylsulfoxide, or dioxan, at temperatures from appropriately 15° C. to appropriately 120° C., preferably at the boil.

When one of $Y_1$ and $Y_2$ denotes a reactive esterified hydroxy group and the other one represents a group of the formula $Y_3$—X— in which $Y_3$ denotes a metallic group such as a halo-magnesium group, the reaction is preferably performed according to Grignard method, wherein the metallic intermediate is preferably formed in situ.

When one of $Y_1$ and $Y_2$ denotes lower alkanoyl and the other one represents lower alkyl, the intermolecular condensation of compounds of the formulae II and III is preferably performed according to the Shaw and Wagstaff method or one of its many modifications.

When one of $Y_1$ and $Y_2$ denotes lower alkanoyl and the other one represents triarylphosphoranylidenemethyl, the condensation is preferably performed according to the well known Wittig olefin-building method, preferably by forming the phosphoranylidene component from a corresponding triarylphosphonium halide in situ, for example, by reacting the latter with a metal base, such as an alkalimetal hydride, such as sodium hydride, or with a metal-organic base, such as a lower alkyl metal compound, such as butyllithium, or with an alkali metal alkanolate, for example, potassium tertiary butoxide, preferably in an inert organic solvent, such as an aromatic or arylaliphatic hydrocarbon, for example, benzene or toluene, at appropriately −10° C. to appropriately 39° C., preferably first at 0° to 10° C. and then at ambient temperature.

Electrofugal groups $Y_4$ are, for example, esterified hydroxy groups, such as hydroxy groups esterified with an organic acid, for example, lower alkanoyloxy or hydroxy groups esterified with an anorganic acid, for example, halo groups, or tertiary amino groups, such as tri-lower alkylamino groups, for example, trimethylamino, or lower-alkyleneamino, lower azaalkyleneamino, loweroxyalkyleneamino or lower thiaalkyleneamino groups, such as pyrrolidino, piperidino, morpholino or thiomorpholino, or corresponding quaternary ammonium groups.

The protection of functional groups by such protecting groups, the protecting groups themselves and the reactions for their removal are described, for example, in standard works.

The elimination of H—$Y_4$ from compounds of formula IV can be performed in a customary manner. Thus, water or lower alkanoic acids may be eliminated by means of azeotropic distillation, for example, in toluene, advantageously under mild-acidic conditions. Hydrogen halides may be removed under basic conditions such as reaction with an alkalimetal alkanolate, preferably in the corresponding lower alkanol as a solvent or co-solvent, or by heating in the presence of a tertiary amine, such as a tri-lower alkylamine.

The starting materials for the above described reactions are generally known. Novel starting materials can be obtained in manner analogous to the methods for the preparation of known starting materials.

Compounds of formula I obtainable in accordance with the process can be converted into different compounds of formula I in customary manner, for example a free carboxy group may be esterified or amidated, an esterified or amidated carboxy group may be converted into a free carboxy group, an esterified carboxy group can be converted into an unsubstituted or substituted carbamoyl group, a free amino group can be acylated or alkylated, and a free hydroxy can be acylated.

Also, compounds of the formula I can be oxidized by customary methods such as reaction with an organic peroxy acid, yielding the corresponding pyridine-N-oxide derivatives.

Salts of compounds of formula I can also be converted in a manner known per se into the free compounds, for example by treatment with a base or with an acid.

Resulting salts can be converted into different salts in a manner known per se.

The compounds of formula I, including their salts, may also be obtained in the form of hydrates or may include the solvent used for crystallization.

As a result of the close relationship between the novel compounds in free form and in the form of their salts, hereinbefore and hereinafter any reference to the free compounds and their salts is to be understood as including the free compounds, as well as the corresponding salts.

In a compound of formula I the configuration at individual chirality centers can be selectively reversed. For example, the configuration of asymmetric carbon atoms that carry nucleophilic substituents, such as amino or hydroxy, can be reversed by second order nucleophilic substitution, optionally after conversion of the bonded nucleophilic substituent into a suitable nucleofugal leaving group and reaction with a reagent introducing the original substituent, or the configuration at carbon atoms having hydroxy groups can be reversed by oxidation and reduction, analogously to European Patent Application EP-A-0 236 734.

The invention relates also to pharmaceutical compositions comprising compounds of formula I.

The pharmacologically acceptable compounds of the present invention may be used, for example, in the preparation of pharmaceutical compositions that comprise an effective amount of the active ingredient together or in a mixture with a significant amount of inorganic or organic, solid or liquid, pharmaceutically acceptable carriers.

The pharmaceutical compositions according to the invention are compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

The pharmaceutical compositions of the present invention are prepared in a manner known per se, for example by means of conventional dissolving, lyophilizing, mixing, granulating or confectioning processes.

The doses to be administered to warm-blooded animals, for example human beings, of, for example, approximately 70 kg body weight, especially the doses effective in disorders caused by or associated with irregularities of the glutamatergic signal transmission, are from approximately 3 mg to approximately 3 g, preferably from approximately 10 mg to approximately 1 g, for example approximately from 20 mg to 500 mg, per person per day, divided preferably into 1 to 4 single doses which may, for example, be of the same size. Usually, children receive about half of the adult dose. The dose necessary for each individual can be monitored, for example by measuring the serum concentration of the active ingredient, and adjusted to an optimum level.

The following non-limiting Examples serve to illustrate the invention; temperatures are given in degrees Celsius, pressures in mbar.

EXAMPLE 1

3-[2-(6-Methylpyridin-2-yl)-vinyl-benzonitrile

A solution of 2,6-dimethyl pyridine (4.2 ml, 36.28 mMol), 3-cyanobenzaldehyde (4.95 g, 37.74 mMol) in acetic anhydride (6.85 ml) is heated under reflux for 16 hours. The acetic anhydride is then evaporated in vacuo and the residue purified on column chromatography (silica gel 400 g). The column is first eluted with toluene (400 ml) and then with toluene/ethyl acetate 95:5. The fractions containing the desired compound are combined, and evaporated in vacuo. The solid residue is recrystallized from methylene chloride/hexane and 3.18 g of white crystals are isolated. (melting point: 91–92°).

EXAMPLE 2

2-[2-(6-Methyl-pyridin-2-yl)-vinyl]-benzonitrile

A solution of 2,6-dimethyl pyridine (5.8 ml, and 50 mMol), and 2-cyanobenzaldehyde (6.81 g, and 52 mMol) in acetic anhydride (9.5 ml) is heated under reflux for 16 hours. The acetic anhydride is then evaporated in vacuo and the residue purified on column chromatography (silica gel 400 g). The column is first eluted with toluene (400 ml) and then with toluene/ethyl acetate 95:5. The fractions containing the desired compound are combined, evaporated in vacuo. The solid residue is recrystallized from methylene chloride/diisopropyl ether and white crystals are isolated. (melting point: 113–114°).

EXAMPLE 3

2-Methyl-6-[2-(pyridin-4-yl)-vinyl]-pyridine

A solution of 2,6-dimethyl pyridine (5.8 ml, and 50 mMol), and pyridine-4-carbaldehyde (4.9 ml, and 52 mMol) in acetic anhydride (9.5 ml) is heated under reflux for 16 hours. The acetic anhydride is then evaporated in vacuo and the residue purified on column chromatography (silica gel 900 g). The column is first eluted with toluene/acetone 4:1 (5 L), then with toluene/acetone 3:1 (5 L) and finally with toluene/acetone 2:1 (15 L). The fractions containing the desired compound are combined, evaporated in vacuo. The solid residue is recrystallized from methylene chloride/diisopropyl ether and 0.956 g of white crystals are isolated. (melting point: 72–73° C.).

EXAMPLE 4

2-Methyl-6-[2-(pyridin-3-yl)-vinyl]-pyridine

A solution of 2,6-dimethyl pyridine (5.8 ml, 50 mMol), pyridine-3-carbaldehyde (4.9 ml, 52 mMol) in acetic anhydride (9.5 ml) is heated under reflux for 10 hours. The acetic anhydride is then evaporated in vacuo and the residue purified on column chromatography (silica gel 900 g). The column is first eluted with toluene/acetone 9:1 (7 L), then with toluene/acetone 4:1 (5 L) and finally with toluene/acetone 2:1 (5 L). The fractions containing the desired compound are combined, and evaporated in vacuo. The solid residue is recrystallized from methylene chloride/diisopropyl ether and 4.28 g of a colorless oil which solidify upon standing at 6–8° C.

EXAMPLE 5

2-[2-(3-Bromophenyl)ethynyl]-6-methyl-pyridine 1.2 g (2.8 mMol) of 2-[1,2-dibromo-2-(3-bromophenyl)-ethyl]-6-methyl-pyridine are dissolved in 10 ml of ethanol. 0.9 g (16.1 mMol) of potassium hydroxide (powder) are added, and the resulting suspension is heated under reflux for 4 hours. The suspension is then cooled to room temperature, poured into 100 ml of brine and extracted thrice with 30 ml each of t-butyl methyl ether. The combined organic phases are washed with 30 ml of brine, dried over Sodium sulfate, filtrated and evaporated in vacua. 0.720 g of the title compound are obtained as a colorless oil crystallizing on standing; melting point 60–61°.

The starting material can be obtained as follows:

a) 2-[2-(3-Bromophenyl)-vinyl]-6-methyl-pyridine

A solution of 24 ml (200 mMol) of 2,6-dimethyl pyridine and 25.6 ml (207 mMol) of 3-bromobenzaidehyde in 38 ml of acetic anhydride is heated under reflux for 7.5 hours. The acetic anhydride is then evaporated in vacuo, and the residue is dissolved in 500 ml of 4N hydrochloric acid and twice extracted with 200 ml each of hexane. The water phase is then extracted four times with 300 ml each of tert.-butyl methyl ether. The combined organic phases are washed twice with 300 ml each of a saturated solution of NaHCO$_3$ in water, then once with 300 ml of brine (300 ml), dried over sodium sulfate, filtrated and evaporated in vacuo yielding 4.2 g of the title compound as colorless crystals of melting point 58–590.

b) 2-[1,2-dibromo-2-(3-bromophenyl)-ethyl]-6-methyl-pyridine 1 g (3.6 mMol) of 2-(3-Bromo-phenylethynyl)-6-methyl-pyridine are dissolved in 5 ml of carbon tetrachloride, and the solution is heated to 55–60°. A solution of 0.23 ml (4.4 mMol) of bromine (Br$_2$) in 1 ml of carbon tetrachloride is added dropwise. The reaction mixture is maintained at 55–60° for 30 minutes and then cooled to room temperature. The resulting precipitate is collected by filtration and dried in vacuo. 1.3 g of the title compound in form of yellow crystals of melting point 164–166 are isolated.

EXAMPLE 6

3-[2-(6-Methylpyridin-2-yl)ethynyl]-benzonitrile

A mixture of 1 g (8.54 mMol) 2-ethynyl-6-methyl-pyridine (prepared in analogy to D. E. Ames et al., Synthesis, 1981, p. 364–5), 2.3 g (12.8 mMol) 3-bromo-benzonitrile, 0.47 g (0.7 mMol) bis-(triphenylphosphine)-palladium-II-chloride, 80 mg (0.41 mMol) cuprous iodide and 1.53 ml (15 mMol) triethylamine in 10 ml dimethylformamide is stirred for 3 hours at 90° C. The reaction mixture is cooled to ambient temperature, poured into water and extracted with dichloromethane. The organic layer is dried over sodium sulfate, filtered, evaporated to dryness and the residue is purified by chromatography on silica gel with hexane/ethyl acetate (4:1) as eluant. Crystallization from hexane of the obtained product affords 0.53 g (28.4%) of the title compound as brown crystals, melting point 120–3° C.

EXAMPLE 7

In analogous manner to Example 1 (when X is alkenylene) or Example 5 (when X is alkynylene), the following compounds of formula I can be prepared:

| Compound of formula I | Melting point (° C.) |
| --- | --- |
| 2-Styryl-pyridin-3-ol | 249–252 |
| 2-Methyl-6-[2-(3-nitro-phenyl)-vinyl]-pyridine | 100–101 |
| 2-[2-(2-Chloro-phenyl)-vinyl -pyridine | colorless oil |
| 2-Methyl-6-styryl-pyridine | 40–42 |
| Acetic acid 6-[2-(2-chloro-phenyl)-vinyl]-pyridin-3-yl ester | 75–77 |
| 6-[2-(2-Chloro-phenyl)-vinyl]-pyridin-3-ol | 168–171 |
| Acetic acid 2-[2-(2-chloro-phenyl)-vinyl]-pyridin-3-yl ester | 99–102 |
| 2-[2-(2-Chloro-phenyl)-vinyl]-pyridin-3-ol | 232–234 |
| 6-Methyl-2-styryl-pyridin-3-ol | 261 dec |
| Acetic acid 2-[2-(2-chloro-phenyl)-vinyl]-6-methyl-pyridin-3-yl ester | 92–94 |
| 2-[2-(2-Chloro-phenyl)-vinyl]-6-methyl-pyridin-3-ol | 232–234 |
| (Z)-6-Methyl-2-styryl-pyridin-3-ol | 145–148 |
| 2-[2-(2-Chloro-phenyl)-vinyl]-6-methyl-pyridine | 51–52 |

| Compound of formula I | Melting point (° C.) |
|---|---|
| 2-[2-(2-Fluoro-phenyl)-vinyl]-pyridine | 69–70 |
| 2-[2-(2-Nitro-phenyl)-vinyl]-pyridine | 97–99 |
| Acetic acid 2-[2-(4-chloro-phenyl)-vinyl]-6-methyl-pyridin-3-yl ester | 102–103 |
| Acetic acid 6-[2-(4-chloro-phenyl)-vinyl]-2-methyl-pyridin-3-yl ester | 130–131 |
| 2-[2-(4-Chloro-phenyl)-vinyl]-6-methyl-pyridin-3-ol | 271–278 dec |
| 6-[2-(4-Chloro-phenyl)-vinyl]-2-methyl-pyridin-3-ol | 265–270 dec |
| Acetic acid 6-methyl-2-[2-(2-nitro-phenyl)-vinyl]-pyridin-3-yl ester | 139–140 |
| 6-Methyl-2-[2-(2-nitro-phenyl)-vinyl]-pyridin-3-ol | 190–195 dec |
| Acetic acid 2-methyl-6-[2-(2-nitro-phenyl)-vinyl]-pyridin-3-yl ester | 99–100 |
| 2-Methyl-6-[2-(2-nitro-phenyl)-vinyl]-pyridin-3-ol | 230–233 dec |
| Acetic acid 2-[2-(3-chloro-phenyl)-vinyl]-6-methyl-pyridin-3-yl ester | 97–99 |
| Acetic acid 6-[2-(3-chloro-phenyl)-vinyl]-2-methyl-pyridin-3-yl ester | 112–114 |
| 2-[2-(3-Chloro-phenyl)-vinyl]-6-methyl-pyridin-3-ol | 232–235 |
| 2-[2-(3-Chloro-phenyl)-vinyl]-6-methyl-pyridin-3-ol | 230–232 |
| (Z)-(6-Styryl-pyridin-2-yl)-methanol | 69–70 |
| (E)-(6-Styryl-pyridin-2-yl)-methanol | 58–60 |
| 2,2'-(1,2-Ethenediyl) bis[6-methyl]-pyridine | 108–110 |
| Dimethyl-[3-(6-methyl-2-styryl-pyridin-3-yloxy)-propyl]-amine; hydrochloride salt | 136–139 |
| (E)-6-[2-(2-Pyridyl)vinyl]-2-picoline | 56–57 |
| 2-Methyl-6-styryl-pyridine 1-oxide | 102–103 |
| 2-Styryl-pyridine 1-oxide | 156–159 |
| (E)-6-Methyl-2-(2-pyridin-2-yl-vinyl)-pyridin-3-ol | 240–242 |
| (Z)-6-Methyl-2-(2-pyridin-2-yl-vinyl)-pyridin-3-ol; HCl salt | 225–228 |
| 6-Styryl-pyridine-2-carbonitrile | 92–93 |
| 2-[2-(2, 6-Dichloro-phenyl)-vinyl]-6-methyl-pyridine | light yell. oil |
| 3-Methoxy-6-methyl-2-styryl-pyridine | light yell. oil |
| 6-Styryl-pyridine-2-carboxylic acid amide | 141–142 |
| 2-[2-(6-Methyl-pyridin-2-yl)-vinyl]-benzonitrile | 113–114 |
| 3-[2-(6-Methyl-pyridin-2-yl)-vinyl]-benzonitrile | 91–92 |
| 4-[2-(6-Methyl-pyridin-2-yl)-vinyl]-benzonitrile | 131–132 |
| 6-Styryl-pyridine-2-carboxylic acid; HCl Salt | 209–212 |
| 6-Styryl-pyridine-2-carboxylic acid methyl ester | 87–88 |
| Acetic acid 2-[2-(6-methyl-pyridin-2-yl) -vinyl]-phenyl ester | colorless oil |
| 2-[2-(6-Methyl-pyridin-2-yl)-vinyl]-phenol | 227–229 |
| Acetic acid 2-methoxy-4-[2-(6-methyl-pyridin-2-yl)-vinyl]-phenyl ester | 102–103 |
| 2-[2-(3-Chloro-phenyl)-vinyl]-6-methyl-pyridine | 59–61 |
| 2-[2-(4-Chloro-phenyl)-vinyl]-6-methyl-pyridine | 83–85 |
| 2-[2-(2-Chloro-phenyl)-vinyl]-5-ethyl-pyridine | 34–35 |
| 1-(6-Styryl-pyridin-2-yl)-ethanone | 67–88 |
| 6-[2-(2-Chloro-phenyl)-vinyl]-2-methyl-nicotinic acid ethyl ester | 80–82 |
| 2-[2-(2-Chloro-phenyl)-vinyl]-6-methyl-nicotinic acid ethyl ester | 70–72 |
| 2-[2-(6-Methyl-pyridin-2-yl)-vinyl]-benzoic acid; HCl salt | 218–219 |
| 3-[2-(6-Methyl-pyridin-2-yl)-vinyl]-benzoic acid | 150–151 |
| 4-[2-(6-Methyl-pyridin-2-yl)-vinyl]-benzoic acid | 206–207 |
| 3-[2-(6-Methyl-pyridin-2-yl)-vinyl]-benzoic acid methyl ester; HCl salt | 237–238 |
| 4-[2-(6-Methyl-pyridin-2-yl)-vinyl]-benzoic acid methyl ester | 112–113 |
| 2-Methoxy-4-[2-(6-methyl-pyridin-2-yl)-vinyl]-phenol | 118–119 |
| {3-[2-(6-Methyl-pyridin-2-yl)-vinyl]-phenyl}-methanol; HCl salt | 230–231 |
| 6-Styryl-pyridine-2-carboxylic acid .tert.-butylamide | 87–88 |
| 2-(2-Bromo-2-vinyl)-6-methyl-pyridine; HCl salt | 150–154 |
| 2-Methyl-6-phenylethynyl-pyridine; HCl salt | 146–148 |
| 6-Styryl-pyridine-2-carboxylic acid hexylamide; HCl salt | 118–125 |
| 6-[2-(2-Chloro-phenyl)-vinyl]-2-methyl-nicotinic acid | 219–221 dec |
| 2-[2-(2-Chloro-phenyl)-vinyl]-6-methyl-nicotinic acid | 168–170 |
| 2-[2-(3,5-Dichloro-phenyl)-vinyl]-6-methyl-pyridine | 75–77 |
| 2-Methyl-6-[2-(3-trifluoromethyl-phenyl)-vinyl]-pyridine | 44–45 |
| (E)-6-[2-(4-pyridyl)vinyl]-2-pocoline | 72–73 |
| N,N-Diethyl-3-[2-(6-methyl-pyridin-2-yl)-vinyl]-benzamide; HCl salt | 227–228 |
| N,N-Diethyl-4-[2-(6-methyl-pryidin-2-yl)-vinyl]-benzamide; HCl salt | 183–184 |
| (E)-8-[2-(3-pyridyl)vinyl]-2-picoline | yellowish oil |
| {2-[2-(2-Chloro-phenyl)-vinyl]-6-methyl-pyridin-3-yloxyl}-acetic acid ethyl ester | colorless gum |
| 3-[2-(6-Methyl-pyridin-2-yl)-vinyl]-.N.-(3-trifluoromethyl-phenyl)-benzamide; HCl salt | 249–251 |
| 4-[2-(6-Methyl-pyridin-2-yl)-vinyl]-.N.-(3-trifluoromethyl-phenyl)-benzamide | 160–161 |
| 2-[2-(3-Nitro-phenyl)-vinyl]-pyridine | 127–128 |
| 6-Styryl-pyridine-2-carboxylic acid (3-trifluoromethyl-phenyl)-amide | 126–129 |
| 2-(6-Styryl-pyridin-2-yl)-propan-2-ol, HCl salt | 171–174 |
| 2-Methyl-6-(2-thiophen-2-yl-vinyl)-pyridine, HCl salt | 208–211 |
| 2-[2-(3-Chloro-phenyl)-vinyl]-pyridine | 51–53 |
| 2-[2-(3-Cyano-phenyl)-vinyl]-pyridine | 85 . 86 |
| 2-[2-(3-Bromo-phenyl)-vinyl]-6-methyl-pyridine | 58–59 |
| 2-[2-(3-Bromo-phenyl)-2-fluoro-vinyl]-6-methyl-pyridine | 58–59 |
| 2-[2-(3,5-Dimethylphenyl)-2-fluoro-vinyl]-6-methyl-pyridine | 70–72 |
| 2-[2-(2,3-Dimethoxy-phenyl)-vinyl]-6-methyl-pyridine | colorless oil |
| 2-[2-(2,3-Dichloro-phenyl)-vinyl]-6-methyl-pyridine | 67–68 |
| 2-[2-(3-Chloro-phenyl)-1-methyl-vinyl]-pyridine | colorless oil |
| {2-[2-(2-Chloro-phenyl)-vinyl]-6-methyl-pyridin-3-yl}-methanol | 87–90 |
| 2-Methyl-6-[2-(3-trimethylsilanylethynyl-phenyl)-vinyl]-pyridine | yellowish oil |
| 2-[2-(3,4-Difluoro-phenyl)-vinyl]-6-methyl-pyridine | 61–62 |
| 2-[2-(3-Ethynyl-phenyl)-vinyl]-6-methyl-pyridine | yellowish oil |
| 2-[2-(3,5-Difluoro-phenyl)-vinyl]-6-methyl-pyridine | yellowish oil |
| 2-[2-(3-Fluoro-phenyl)-vinyl]-6-methyl-pyridine | yellowish oil |
| 2-[2-(3-Methoxy-phenyl)-vinyl]-6-methyl-pyridine | yellowish oil |
| 2-Methyl-6-[2- (3-phenoxy-phenyl)-vinyl]-pyridine | yellowish oil |
| 2-[2-(3-Benzyloxy-phenyl)-vinyl]-6-methyl-pyridine | 68–69 |
| 2-[2-(2,5-Difluoro-phenyl)-vinyl]-6-methyl-pyridine | 44–45 |
| {2-[2-(2-Chloro-phenyl)-vinyl]-6-methyl-pyridin-3-yloxy}-acetic acid | 230–233 |
| (3-{2-[2-(3-Chloro-phenyl)-vinyl]-6-methyl-pyridin-3-yloxy}-propyl)-dimethyl-amine | 203–205 |
| {6-[2-(2-Chloro-phenyl)-vinyl]-2-methyl-pyridin-3-yl}methanol | 131–133 |
| 2-(3-Bromo-phenylethynyl)-6-methyl-pyridine | 61–63 |
| 2-Methyl-6-}2-[3-(3-trifluoromethyl-phenoxy)-phenyl]-vinyl}-pyridine | yellowish oil |
| 2-[2-(3,5-Dimethoxy-phenyl)-vinyl]-6-methyl-pyridine | 43–45 |
| 2-[2-(3-Chloro-phenyl)-vinyl]-3-methoxy-6-methyl-pyridine | 52–53 |
| Acetic acid 4-bromo-2-[2-(6-methyl-pyridin-2-yl)-vinyl]-phenyl ester | yellowish oil |
| Acetic acid 3-[2-(6-methyl-pyridin-2-yl)-vinyl]-phenyl ester | yellowish oil |
| 2-[2-(3,4-Dichloro-phenyl)-vinyl]-6-methyl-pyridine | 73–75 |
| 4-Bromo-2-[2-(6-methyl-pyridin-2-yl)-vinyl]-phenol | 246–248 |
| Acetic acid 2-[2-(3,5-dichloro-phenyl)-vinyl]-6-methyl-pyridin-3-yl ester | 156–158 |
| Acetic acid 6-[2-(3,5-dichloro-phenyl)-vinyl]-2-methyl-pyridin-3-yl ester | 159–161 |
| Acetic acid 2-[2-(3,5-dichloro-phenyl)-vinyl]-pyridin-3-yl ester | 154–156 |
| 2-Methyl-6-(2-naphthalen-1-yl-vinyl)-pyridine | yellowish oil |
| 2-[2-(2,3-Dihydro-benzo[1,4]dioxin-6-yl)-vinyl]-6-methyl-pyridine | 99–101 |
| 2-Methyl-6-(2-naphthalen-2-yl-vinyl)-pyridine | 97–99 |

-continued

| Compound of formula I | Melting point (° C.) |
|---|---|
| 2-Methyl-6-(2-m-tolyl-vinyl)-pyridine | yellowish oil |
| 2-{2-[3-(3,5-Dichloro-phenoxy)-phenyl]-vinyl}6-methyl-pyridine | yellowish gum |
| 2-[2-(3-Chloro-phenyl)-propenyl]-6-methyl-pyridine | yellowish oil |
| 2-[2-(2,3-Dihydro-benzofuran-5-yl)-vinyl]-6-methyl-pyridine | 88–90 |
| 2-[2-(4-Fluoro-phenyl)-vinyl]-6-methyl-pyridine | 50–51 |
| 2-Methyl-6-(2-o-tolyl-vinyl)-pyridine | yellowish oil |
| 2-Methyl-6-(2-p-tolyl-vinyl)-pyridine | 85–86 |
| 2-Methyl-6-(2-p-tolyl-propenyl)-pyridine | yellowish oil |
| 3-[2-(6-Methyl-pyridin-2-yl)-vinyl]-phenylamine | 126–129 |
| (2,3-Dimethoxy-7-nitro-quinoxalin-5-ylmethyl)-{3-[2-(6-methyl-pyridin-2-yl)-vinyl]-phenyl}-amine | pale orange foam |
| N-{3-[2- (6-Methyl-pyridin-2-yl)-vinyl]-phenyl}-acetamide | 147 |
| N-{3-[2- (6-Methyl-pyridin-2-yl)-vinyl]-phenyl}2-phenyl-acetamide | 156 |
| 2,2-Dimethyl-N-{3-[2-6-methyl-pyridin-2-yl)-vinyl]-phenyl}-propionamide | 166–168 |
| Thiophene-2-carboxylic acid {3-[2-(6-methyl-pyridin-2-yl)-vinyl]-phenyl}-amide | 197 dec |
| Cyclohexanecarboxylic acid {3-[2-(6-methyl-pyridin-2-yl)-vinyl]-phenyl}-amide | 215 |
| 1-(4-Bromo-phenyl)-3-}3-[2-(6-methyl-pyridin-2-yl)-vinyl]-phenyl}-urea | 197 dec |
| 2-Methyl-6-[2-(4-nitro-phenyl)-vinyl]-pyridine | 134–135 |
| 4-[2-(6-Methyl-pyridin-2-yl)-vinyl]-phenylamine | 147–148 |
| 2-[2-(3,5-Dichloro-phenyl)-vinyl]-6-methyl-pyridin-3-ol | 218–220 |
| 6-[2-(3,5-Dichloro-phenyl)-vinyl]-2-methyl-pyridin-3-ol | 286 dec |
| 2-[2-(3,5-Dichloro-phenyl)-vinyl]-pyridin-3-ol | 240–242 |
| 2-[2-(6-Chloro-benzo[1,3]dioxol-5-yl)-vinyl]-6-methyl-pyridine | 131–132 |
| 2-[2-(2,3-Difluoro-phenyl)-vinyl]-6-methyl-pyridine | 55–56 |
| 2-[2-(3,4-Dichloro-phenyl)-propenyl]-6-methyl-pyridine | yellowish oil |
| 2-[2-(3,5-Bis-trifluoromethyl-phenyl)-vinyl]-6-methyl-pyridine | 85–86 |
| Acetic acid 2-methoxy-6-[2-(6-methyl-pyridin-2-yl)-vinyl]-phenyl ester | yellowish oil |
| 2-Methoxy-6-[2-(6-methyl-pyridin-2-yl)-vinyl]-phenol | 118–120 |
| 2-Methyl-6-[2-(2,3,6-trifluoro-phenyl)-vinyl]-pyridine | 59–62 |
| 2-[2-(4-Fluoro-3-trifluoromethyl-phenyl)-vinyl]-6-methyl-pyridine | yellowish oil |
| 2-Methyl-6-(2,3,6-trifluoro-phenylethynyl)-pyridine | 93–94 |
| Acetic acid 4-chloro-2-[2-(6-methyl-pyridin-2-yl)-vinyl]-phenyl ester | yellowish oil |
| Acetic acid 2,6-di-.tert.-butyl-4-[2-(6-methyl-pyridin-2-yl)-vinyl]-phenyl ester | 127–128 |
| 3-(6-Methyl-pyridin-2-ylethynyl)-benzamide | 187–189 |
| Acetic acid 4-bromo-2-methoxy-6-[2-(6-methyl-pyridin-2-yl)-vinyl]-phenyl ester | 151–153 |
| 2-(6-Chloro-benzo[1,3]dioxol-5-ylethynyl)-6-methyl-pyridine | 105–106 light brown crystals |
| 2-[2-(3,5-Dichloro-phenyl)-vinyl]-3-methoxy-6-methyl-pyridine | 127–129 |
| 2-[2-(3,5-Dichloro-phenyl)-vinyl]-3-methoxy-pyridine | 111–113 |
| 5-Azido-2-[2-(6-methyl-pyridin-2-yl)-vinyl]-phenol | 143 dec |
| 2-[2-(Pyridin-3-yl)ethynyl]-6-methyl-pyridine | light yellow crystals 60–61 |
| N-{3-[2-(6-Methyl-pyridin-2-yl)-vinyl]-phenyl}-succinamic acid | 212–213 |
| 1-tert.-Butyl-3-{3-[2-(6-methyl-pyridin-2-yl)-vinyl]-phenyl}-urea | 191–192 |
| 5-({3-[2-(6-Methyl-pyridin-2-yl)-vinyl]-phenylamino}-methyl)-7-nitro-1,4-dihydro-quinoxaline-2,3-dione | 250 dec |
| Tetrahydro-furan-2-carboxylic acid {3-[2-(6-methyl-pyridin-2-yl)-vinyl]-phenyl}-amide | 160–161 |
| (1-{3-[2-(6-Methyl-pyridin-2-yl)-vinyl]-phenylcarbamoyl}-2-phenyl-ethyl)-carbamic acid tert.-butyl ester | colorless foam |
| ({3-[2-(6-Methyl-pyridin-2-yl)-vinyl]-phenylcarbamoyl}-methyl)-carbamic acid tert.-butyl ester | colorless foam |
| Diethyl-{3-[2-(6-methyl-pyridin-2-yl)-vinyl]-phenyl}-amine | 217 dec |
| Ethyl-{3-[2-(6-methyl-pyridin-2-yl)-vinyl]-phenyl}amine | 225 dec |
| Ethyl-{3-[2-(6-methyl-pyridin-2-yl)-vinyl]-phenyl}amine | 183 dec |
| 2-(2-Ethoxy-3,6-difluoro-phenylethynyl)-6-methyl-pyridine | yellowish oil |
| 2-(3,5-Difluoro-phenylethynyl)-6-methyl-pyridine | yellowish oil |
| 2-(3-Fluoro-phenylethynyl)-6-methyl-pyridine | 26–28 |
| 2-[2-(3,5-Dimethyl-phenyl)-vinyl]-6-methyl-pyridine | 56–57 |
| 2-[2-(3,4-Dimethoxy-phenyl)-vinyl]-6-methyl-pyridine | 55–56 |
| 2-(3,4-Dichloro-phenylethynyl)-6-methyl-pyridine | 73–74 |
| 2-(4-Ethoxy-3-trifluoromethyl-phenylethynyl)-6-methyl-pyridine | 61–62 |
| 2-(4-Fluoro-phenylethynyl)-6-methyl-pyridine | 98–100 |
| 2-Methyl-6-.o.tolylethynyl-pyridine | yellowish oil |
| 2-(3,4-Difluoro-phenylethynyl)-6-methyl-pyridine | 65–68 |
| 2-Methyl-6-[2-(2,3,5-trichloro-phenyl)-vinyl]-pyridine | 80–82 |
| 1[3-(6-Methyl-pyridin-2-ylethynyl)-phenyl]-ethanone | 76–78 |
| 2-Methyl-6-(3-trifluoromethyl-phenylethynyl)-pyridine | 35–37 |
| 2-Methyl-6-(3-nitro-phenylethynyl)-pyridine | 99.5–102.5 |
| 6-[2-(3,5-Dichloro-phenyl)-vinyl]-3-methoxy-2-methyl-pyridine | 98–100 |
| {2-[2-(2-Chloro-phenyl)-vinyl]-6-methyl-pyridin-3-yl}-morpholin-4-yl-methanone | 123–125 |
| (3-{2-[2-(3,5-Dichloro-phenyl)-vinyl]-6-methyl-pyridin-3-yloxy}-propyl)-dimethyl-amine hydrochloride salt | 207–210 |
| N-{4-[2-(6-Methyl-pyridin-2-yl)-vinyl]-phenyl}-succinamic acid | 201 dec |
| N-{4-[2-(6-Methyl-pyridin-2-yl)-vinyl]-phenyl}-2-phenyl-acetamide | 236–237 dec |
| ({4-[2-(6-Methyl-pyridin-2-yl)-vinyl]-phenylcarbamoyl}-methyl)-carbamic acid .tert.-butyl ester | 144–145 dec |
| 1-tert.-Butyl-3-{4-[2-(6-methyl-pyridin-2-yl)-vinyl]-phenyl}-urea | 209 dec |
| {3-[2-(6-Methyl-pyridin-2-yl)-vinyl]-phenyl}-thiophen-2-ylmethyl-amine hydrochloride salt | 161–162 |
| Cyclohexylmethyl-{3-[2-(6-methyl-pyridin-2-yl)-vinyl]-phenyl}-amine hydrochloride salt | 178–179 dec |
| {4-[2-(6-Methyl-pyridin-2-yl)-vinyl]-phenyl}-thiophen-2-ylmethyl-amine | 100 |
| Cyclohexylmethyl-{4-[2-(6-methyl-pyridin-2-yl)-vinyl]-phenyl}-amine | 106–167 |
| 2-Amino-N-{3-[2-(6-methyl-pyridin-2-yl)-vinyl]-phenyl}-3-phenyl-propionamide | 102 |
| 2-Amino-N-{3-[2-(6-methyl-pyridin-2-yl)-vinyl]-phenyl}-acetamide | 105 |
| 2-Amino-N-{4-[2-(6-methyl-pyridin-2-yl)-vinyl]-phenyl}-acetamide | 217–219 dec |
| 1-[1-({2-[2-(2-Chloro-phenyl)-vinyl]-6-methyl-pyridin-3-yloxy}-acetyl)-piperidin-4-yl]-imidazolidin-2-one | amorphous foam |
| (1-{4-[2-(6-Methyl-pyridin-2-yl)-vinyl]-phenylamino}-ethyl)-phosphonic acid dimethyl ester | orange amorphous solid |
| 2-[2-(2-Methoxy-phenyl)-vinyl]-6-methyl-pyridine | 129–130 |
| 2-(3-Ethoxy-4-fluoro-phenylethynyl)-6-methyl-pyridine | 82–83 |
| 2-(3-Chloro-phenylethynyl)-6-methyl-pyridine | 57–59 |
| 1-(3-Pyridin-2-ylethynyl-phenyl)-ethanone | 48–51 |
| 4-Chloro-2-[2-(6-methyl-pyridin-2-yl)-vinyl]-phenol | 256–260 |
| 4-Bromo-2-methoxy-6-[2-(6-methyl-pyridin-2-yl)-vinyl]-phenol | 121–123 |
| 2-Methyl-6-.m.-tolylethynyl-pyridine | 57–58 |
| 2-(2,5-Difluoro-phenylethynyl)-6-methyl-pyridine | 49–50 |
| 2-(3,5-Dimethyl-phenylethynyl)-6-methyl-pyridine | yellowish oil |
| 2-[2-(3,5-Dibromo-phenyl)-vinyl]-6-methyl-pyridine | 68–70 |
| 2-Methyl-6-[2-(pyrimidin-5-yl)-ethynyl]-pyridine | 110–112 |
| (2-{2-[2-(3-Chloro-phenyl)-vinyl]-6-methyl-pyridin-3-yloxy}-ethyl)-dimethyl-amine | 165–167 |

| Compound of formula I | Melting point (° C.) |
| --- | --- |
| Acetic acid 1-{4-[2-(6-methyl-pyridin-2-yl)-vinyl]-phenyl}-ethyl ester | |
| 3-(6-Methyl-pyridin-2-ylethynyl)-phenylamine | 129–130 |
| N-[3-(6-Methyl-pyridin-2-ylethynyl)-phenyl]-2-phenyl-acetamide | 133–135 dec |
| Thiophene-2-carboxylic acid [3-(6-methyl-pyridin-2-ylethynyl)-phenyl]-amide | 156–157 dec |
| 2-Methyl-6-(thiophen-2-ylethynyl)-pyridine | 34–36 |
| 3-(6-Methyl-pyridin-2-ylethynyl)-benzoic acid ethyl ester | 56–58 |
| 2-(3,5-Dibromo-phenylethynyl)-6-methyl-pyridine | 100:101 |
| {2-[2-(2-Chloro-phenyl)-vinyl]-6-methyl-pyridin-3-ylmethyl}-dimethyl-amine | 227–229 dec |
| (3-{6-[2-(3-Chloro-phenyl)-vinyl]-2-methyl-pyridin-3-yloxy}-propyl)-dimethyl- | 184–186 |
| 5-Azido-4-iodo-2-[2-(6-methyl-pyridin-2-yl)-vinyl]-phenol | red glass |
| 2,6-Di-tert-butyl-4-[2-(6-methyl-pyridin-2-yl)-vinyl]-amino; HCl salts phenol | 126–127 |
| 1-{4-[2-(6-Methyl-pyridin-2-yl)-vinyl]-phenyl}-ethanol | 97–99 |
| 2-Methyl-6-[2-(pyrimidin-2-yl)-ethynyl]-pyridine | 144–145 |
| [3-(6-Methyl-pyridin-2-ylethynyl)-phenyl]-phenyl-methanone | 99–100 |
| 6-(6-Methyl-pyridin-2-ylethynyl)-3,4-dihydro-1H-quinolin-2-one | 189–191 |
| 2-(3-{2-[2-(3-Chloro-phenyl)-vinyl]-6-methyl-pyridin-3-yloxy}-propyl)-isoindol-1,3-dione | 101–103 |
| 3-Methoxy-6-methyl-2-.m.-tolylethynyl-pyridine | brown oil |
| Acetic acid 2-[2-(6-methyl-pyridin-2-yl)-vinyl]-4-nitro-phenyl ester | 129–131 |
| 6-(6-Methyl-pyridin-2-ylethynyl)-indan-1-one | 160–165 |
| 2-Methyl-6-[2-(pyrazin-2-yl)-ethynyl]-pyridine | 95–96 |
| N-Methyl-N-(3-{4-[2-(6-methyl-pyridin-2-yl)-vinyl]-phenoxy}-propyl)-acetamide | 62–70 |
| 2-[2-(3,5-Bis-trifluoromethyl-phenyl)-1-ethoxy-vinyl]-6-methyl-pyridine | yellow oil |
| Acetic acid 2-phenylethynyl-pyridin-3-yl ester | brown oil |
| Acetic acid 6-methyl-2-.m.-tolylethynyl-pyridin-3-yl ester | brown oil |
| Acetic acid 4-[2-(6-methyl-pyridin-2-yl)-vinyl]-2-nitro-phenyl ester | 91–93 |
| 2-[2-(6-Methyl-pyridin-2-yl)-vinyl]-4-nitro-phenol | 275 dec |
| Dimethyl-[3-(2-phenylethynyl-pyridin-3-yloxyl-propyl]-amine | yellowish oil |
| Dimethyl-(3-{4-[2-(6-methyl-pyridin-2-yl)-vinyl]-phenoxy}-propyl)-amine | 240–243 |
| 1-{4-[2-(6-Methyl-pyridin-2-yl)-vinyl]-phenyl}-ethanone | 56–58 |
| 2-(3-Fluoro-phenylethynyl)-quinoline | 81–83 |
| Acetic acid 2-methyl-6-styryl-pyridin-3-yl ester | 93–96 |
| 4-[2-(6-Methyl-pyridin-2-yl)-vinyl]-2-nitro-phenol | 141–143 |
| 3-Ethoxy-4-[2-(6-methyl-pyridin-2-yl)-vinyl]-2-nitro-phenol | 175–178 dec |
| 4-(6-Methyl-pyridin-2-ylethynyl)-2-nitro-phenol | 184–187 dec |
| Acetic acid 2-[2-(6-methyl-pyridin-2-yl)-vinyl]-6-nitro-phenyl ester | 105–110 dec |
| Dimethyl-[3-(6-methyl-2-phenylethynyl-pyridin-3-yloxy)-propyl]-amine | yellow gum |
| 2-Azido-4-[2-(6-methyl-pyridin-2-yl)-vinyl]-phenol | 155–157 dec |
| Dimethyl-[3-(6-methyl-2-.m.-tolylethynyl-pyridin-3-yloxy)-propyl]-amine | yellowish oil |
| 2-(3-Methanesulfonyl-phenylethynyl)-6-methyl-pyridine | 108–110 dec |
| 3-{2-[2-(3-Chloro-phenyl)-vinyl]-6-methyl-pyridin-3-yloxy}-propylamine | 186–189 |
| 4-Azido-.N.-(3-{2-[2-(3-chloro-phenyl)-vinyl]-6-methyl-pyridin-3-yloxy}-propyl)-2-hydroxy-benzamide | 99–102 dec |
| 3-[3-(3-Dimethylamino-propoxy)-6-methyl-pyridin-2-ylethynyl]-benzonitrile | yellow gum |
| 5-(6-Methyl-pyridin-2-ylethynyl)-indan-1-one | 133–134 |
| 2-Methyl-6-(2,3,5-trichloro-phenylethynyl)-pyridine | 112–114 |
| 2-[2-(6-methyl-pyridin-3-yl)ethynyl]-6-methyl-pyridine | 118–119 |
| Dimethyl-{3-[6-methyl-2-(3-trifluoromethyl-phenylethynyl-pyridin-3-yloxy)-propyl]-amine | yellow gum |
| 2-[2-(6-methyl-pyridin-3-yl)ethynyl]-3-methoxy 6-methyl-pyridine hydrochloride salt | 198–199 |
| 2-Methyl-6-(5,6,7,8-tetrahydro-naphthalen-2-ylethynyl)-pyridine | 50–51 |
| 3-[2-(3-Chloro-phenylethynyl)-6-methyl-pyridin-3-yloxy]-propylamine | 151–153 |
| (3-{4-Bromo-2-methoxy-6-[2-(6-methyl-pyridin-2-yl)-vinyl]-phenoxy}-propyl)-dimethyl-amine; | 211–215 |
| [6-(3-Fluoro-phenylethynyl)-pyridin-2-yl]-dimethyl-amine | brown oil |
| 6'-(3-Fluoro-phenylethynyl)-3,4,5,6-tetrahydro-2.H.-[1,2] bipyridinyl | brown gum |
| {3-[2-(3-Chloro-phenylethynyl)-6-methyl-pyridin-3-yloxy]-propyl}-dimethyl-amine | 158–160 |
| 4-Azido-.N.-{3-[2-(3-chloro-phenylethynyl)-6-methyl-pyridin-3-yloxy]-propyl}-2-hydroxy-benzamide | 161–163 dec |
| 1-[3-(6-Methyl-pyridin-2-ylethynyl)-phenyl]-1H-[1,2,4]triazole-3-carboxylic acid ethyl ester | 105–110 dec |
| 1-[3-(6-Methyl-2-phenylethynyl)-pyridin-3-yloxy)-propyl]-piperidin-4-ol | 108–109 |
| 2-Ethynyl-6-(3-fluoro-phenylethynyl)-pyridine | 89–90 |
| 3-Methyl-6-(6-methyl-pyridin-2-ylethynyl)-3H-benzooxazol-2-one | 172–174 |
| 1-[3-(6-Methyl-pyridin-2-ylethynyl)-phenyl]-1H-[1,2,4]triazole-3-carboxylic acid dimethylamide | 154–157 |
| 1-[3-(6-Methyl-2-phenylethynyl)-pyridin-3-yloxy)-propyl]-piperidin-4-ol | amorphous white solid |
| 5-(6-Methyl-pyridin-2-ylethynyl)-2-nitro-phenol | 150–151 dec |
| 5-[2-Bromo-2-(6-methyl-pyridin-2-yl)-vinyl]-2-nitro-phenol | 158–159 |
| 5-[2-(6-Methyl-pyridin-2-yl)-E-vinyl]-2-nitro-phenol | 171–173 |
| 5-[2-(6-Methyl-pyridin-2-yl)-Z-vinyl]-2-nitro-phenol | 108–110 |
| 4-Azido-2-hydroxy-.N.-[3-(6 -methyl-pyridin-2-ylethynyl)-phenyl]-benzamide | 180–182 dec |
| 5-(3-Dimethylamino-propoxy)-6-phenylethynyl-pyridine-2-carboxylic acid ethyl ester | 160–162 |
| 6-Methyl-2-styryl-pyrimidin-4-ol | 221–225 |
| 2-Ethyl-6-(3-fluoro-phenylethynyl)-pyridine | brown oil |
| 2-(3,5-Dichloro-phenylethynyl)-6-methyl-pyridine | 74–76 |
| 2-Methyl-6-(3-trifluoromethoxy-phenylethynyl)-pyridine | <30; brown crystals |
| 2-Methyl-6-(3-[1,2,4]triazol-1-yl-phenylethynyl)-pyridine | 128–130 |
| 4-(6-Methyl-pyridin-2-ylethynyl)-phthalonitrile | 138–140 |
| 2-Methyl-6-{2-[3-(1.H.-tetrazol-5-yl)-phenyl]-vinyl}-pyridine; compound with formic acid | 234–240 |
| 3-[2-(3,5-Dichloro-phenylethynyl)-6-methyl-pyridin-3-yloxy]-propylamine | 97–100 |
| {3-[2-(3,5-Dichloro-phenylethynyl)-6-methyl-pyridin-3-yloxy]-propyl}-dimethyl-amine | 171–173 |
| 2-(3,5-Dimethyl-phenylethynyl)-3-methoxy-6-methyl-pyridine | yellowish oil |
| 2-[2-(3-Fluoro-phenyl)-vinyl]-6-methyl-pyridin-3-ol | 251–253 Dec. |
| 6-(3-Fluoro-phenylethynyl)-2-methyl-nicotinic acid ethyl ester | 84–86 |
| 2-Azido-5-(6-methyl-pyridin-2-ylethynyl)-phenol | 153–155 dec |
| 6-(3,4-Dimethoxy-phenylethynyl)-5-(3-dimethylamino-propoxyl-pyridine-2-carboxylic acid ethyl ester | 149–152 |
| 2-(4-Methoxy-3-trifluoromethyl-phenylethynyl)-6-methyl-pyridine | 86–87 |
| 2-(3-Fluoro-phenylethynyl)-6-methoxy-pyridine | brown oil |
| 2-(3-Fluoro-phenylethynyl)-5-methyl-pyridine | 74–76 |
| 6-(3,5-Dichloro-phenylethynyl)-5-(3-dimethylamino-propoxy)-pyridine-2-carboxylic acid ethyl ester | 195–198 |
| 5-(3-Dimethylamino-propoxy)-6-(3,5-dimethyl-phenylethynyl)-pyridine-2-carboxylic acid ethyl ester | 187–190 |
| 6-(3-Fluoro-phenylethynyl)-2-methyl-nicotinic acid | 173–175 |
| [6-(3-Fluoro-phenylethynyl)-2-methyl-pyridin-3-yl]-methanol | 116–118 |
| [4-(4-Fluoro-benzoyl)-piperidin-1-yl]-[6-(3-fluoro-phenylethynyl)-2-methyl-pyridin-3-yl]-methanone | 138–140 |
| 2-(3-Fluoro-phenylethynyl)-6-methyl-nicotinic acid ethyl ester | brown oil |
| 2-(3-Fluoro-phenylethynyl)-4,6-dimethyl-pyridine | brown oil |
| 6-(3-Fluoro-phenylethynyl)-.N.-(5-methoxy-indan-2-ylmethyl)-2-methyl-nicotinamide | 157–159 |
| {[6-(3-Fluoro-phenylethynyl)-2-methoxy-pyridine-3-carbonyl]-amino}-phenyl-acetic acid methyl ester | 133–135 |
| 2-Methyl-6-(5-methyl-thiophen-2-ylethynyl)-pyridine | 58–59 |

-continued

| Compound of formula I | Melting point (° C.) |
|---|---|
| 2-Methyl-6-(2,3,5-trimethyl-phenylethynyl)-pyridine | brown oil |
| 3-{2-[2-(3-Fluoro-phenyl)-vinyl]-6-methyl-pyridin-3-yloxy}-propan-1-ol | 86–88 |
| [6-(3-Fluoro-phenylethynyl)-2-methyl-pyridin-3-ylmethyl]-dimethyl-amine | 220–222 |
| 2,2-Dimethyl-propionic acid 3-[2-(3-fluoro-phenylethynyl)-6-methyl-pyridin-3-yloxy]-propyl ester | yellowish oil |
| 2-Azido-4-iodo-5-(6-methyl-pyridin-2-ylethynyl)-phenol | 140 dec |
| 6-Azido-2,4-diiodo-3-(6-methyl-pyridin-2-ylethynyl)-phenol | 162 dec |
| 4-Azido-2-hydroxy-5-iodo-.N.-[3-(6-methyl-pyridin-2-ylethynyl)-phenyl]-benzamide | 185 dec |
| Acetic acid 3-acetoxymethyl-5-(6-methyl-pyridin-2-ylethynyl)-benzyl ester | brown oil |
| (Benzyl-{[2-(3-fluoro-phenylethynyl)-6-methyl-pyridin-3-yloxy]-acetyl}-amino)-acetic acid ethyl ester | brown oil |
| 2-[2-(3-Fluoro-phenyl)-vinyl]-6-methyl-isonicotinic acid ethyl ester | 76–77 |
| 3-[2-(3-Fluoro-phenylethynyl)-6-methyl-pyridin-3-yloxy]-propan-1-ol | 72–74 |
| [3-Hydroxymethyl-5-(6-methyl-pyridin-2-ylethynyl)-phenyl]-methanol | 115–117 |
| (3-[2-[2-(3,5-Dimethyl-phenyl)-vinyl]-6-methyl-pyridin-3-yloxy}-propyl)-dimethyl-amine | yellowish gum |
| [4-(4-Fluoro-benzoyl)-piperidin-1-yl]-{6-[2-(3-fluoro-phenyl)-vinyl]-2-methyl-pyridin-3-yl}-methanone | 156–158 |
| 2-[2-(3-Fluoro-phenyl)-vinyl]-6-methyl-isonicotinic acid | 245–248 |
| {6-[2-(2-Chloro-phenyl)-vinyl]-2-methyl-pyridin-3-yl}-[4-(4-fluoro-benzoyl)-piperidin-1-yl]-methanone | 109–112 |
| 2-(3-Ethynyl-phenylethynyl)-6-methyl-pyridine | 48–49 |
| (3-{2-[2-(2,6-Dichloro-phenyl)-vinyl]-6-methyl-pyridin-3-yloxy}-propyl)-dimethyl-amine hydrochloride salt | 207–210 |
| (3-{2-[2-(2,3-Dichloro-phenyl)-vinyl]-6-methyl-pyridin-3-yloxy}-propyl)-dimethyl-amine-hydrochloride salt | 161–169 |
| 4-[6-(3-Fluoro-phenylethynyl)-2-methyl-pyridine-3-carbonyl]-piperazine-1-carboxylic acid .tert.-butyl ester | 97–99 |
| [6-(3-Fluoro-phenylethynyl)-2-methyl-pyridin-3-yl]-piperazin-1-yl-methanone | 250–252 dec |
| [4-(4-Azido-2-hydroxy-benzoyl)-piperazin-1-yl]-[6-(3-fluoro-phenylethynyl)-2-methyl-pyridin-3-yl]-methanone | 186–188 dec |
| (3-[2-[2-(2,4-Dichloro-phenyl)-vinyl]-6-methyl-pyridin-3-yloxy}-propyl)-dimethyl-amine hydrochloride salt | 170–176 |
| 2-(3-Fluoro-phenylethynyl)-6-methyl-isonicotinic acid ethyl ester | 89–91 |
| 2-(3-Fluoro-phenylethynyl)-6-methyl-isonicotinic acid .tert.-butyl ester | 94–96 |
| 2-(3-Fluoro-phenylethynyl)-6-methyl-isonicotinic acid | 231 dec |
| [2-(3-Fluoro-phenylethynyl)-6-methyl-pyridin-4-yl)-methanol | 143–146 |
| [4-(4-Fluoro-benzoyl)-piperidin-1-yl]-[2-(3-fluoro-phenylethynyl)-6-methyl-pyridin-4-yl]-methanone | 156–158 |
| 3-Allyloxy-2-[2-(3,5-dichloro-phenyl)-vinyl]-6-methyl-pyridine | 105–106 |
| [2-(3-Fluoro-phenylethynyl)-6-methyl-pyridin-4-yl]-morpholin-4-yl-methanone | 114–116 |
| Acetic acid 3-(6-methyl-pyridin-2-ylethynyl)-benzyl ester | brown oil |
| [2-(3-Fluoro-phenylethynyl)-6-methyl-pyridin-4-ylmethyl]-dimethyl-amine | 209–212 |
| (3-{2-[2-(3,5-Dichloro-phenyl)-propenyl]-6-methyl-pyridin-3-yloxy}-propyl)-dimethyl-amine hydrochloride salt | 182–184 |
| 2-(3-Fluoro-phenylethynyl)-3-methoxy-6-methyl-pyridine | yellowish oil |
| (3-{2-[2-(3,5-Dichloro-phenyl)-vinyl]-pyridin-3-yloxy}-propyl)-dimethyl-amine hydrochloride salt | 171–174 |
| (4-Azido-2-hydroxy-5-iodo-phenyl)-{4-[6-(3-fluoro-phenylethynyl)-2-methyl-pyridine-3-carbonyl]-piperazin-1-yl}-methanone | 195–200 dec |
| 4-Azido-.N.-{3-[2-(3-chloro-phenylethynyl)-6-methyl-pyridin-3-yloxy]-propyl}-2-hydroxy-5-iodo-benzamide | 142–150 dec |
| 4-(2-Pyridin-2-yl-vinyl)-benzoic acid ethyl ester | 100–102 |
| (3-{2-[2-(4-Chloro-phenyl)-vinyl]-6-methyl-pyridin-3-yloxy}-propyl)-dimethyl-amine hydrochloride salt | 159–171 |
| [3-(6-Methyl-pyridin-2-ylethynyl)-phenyl]-methanol | 43–45 |
| 6-(3-Fluoro-phenylethynyl)-nicotinic acid .tert.-butyl ester | 98–93 |
| (3-{2-[2-(3,4-Dichloro-phenyl)-vinyl]-6-methyl-pyridin-3-yloxy}-propyl)-dimethyl-amine hydrochloride salt | 174–177 |
| 2-(1-Bromo-2-phenyl-vinyl)-4-methyl-pyrimidine | yellow oil |
| 6-(3-Fluoro-phenylethynyl)-nicotinic acid | 223 dec. |
| [4-(4-Fluoro-benzoyl)-piperidin-1-yl]-[6-(3-fluoro-phenylethynyl)-pyridin-3-yl]-methanone | 136.0–139.0 |
| 2-(2-.tert.-Butoxy-3,6-difluoro-phenylethynyl)-6-methyl-pyridine | 72.0–74.0 |
| 2-Methyl-6-[2-(2,4,5-trifluoro-phenyl)-vinyl]-pyridine | 74–76 |
| 2-Methyl-6-[2-(2,3,4-trifluoro-phenyl)-vinyl]-pyridine | 79–82 |
| 3-(6-Methyl-pyridin-2-ylethynyl)-phenol | 142–144 |
| 2-Methyl-6-[2-(3,4,5-trifluoro-phenyl)-vinyl]-pyridine | 74–76 |
| 2-(3-Methoxy-phenylethynyl)-6-methyl-pyridine | 55–57 |
| 2-Methyl-6-(2,3,4-trifluoro-phenylethynyl)-pyridine | 104–106 |

(dec = decomposition)

What is claimed is:

1. A compound of formula I

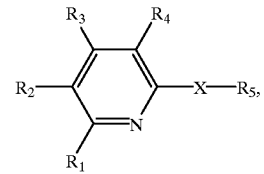

(I)

wherein

X represents an optionally halo-substituted ($C_{2-4}$) alkynylene group bonded via vicinal unsaturated carbon atoms, $R_1$ is ($C_{1-4}$) alkyl, ($C_{1-4}$)alkoxy, hydroxy($C_{1-4}$)alkyl, cyano, ethynyl, carboxy, ($C_{1-4}$)alkoxycarbonyl, di($C_{1-4}$)alkylamino, ($C_{1-6}$)alkylaminocarbonyl, trifluoromethylphenylaminocarbonyl, $R_2$ is hydrogen, hydroxy, ($C_{1-4}$) alkyl, hydroxy ($C_{1-4}$) alkyl, ($C_{1-4}$) alkoxy, carboxy, ($C_{2-5}$)alkanoyloxy, ($C_{1-4}$) alkoxycarbonyl, di($C_{1-4}$)alkylamino($C_{1-4}$)alkanoyl, di($C_{1-4}$)alkylaminomethyl, 4-(4-fluoro-benzoyl)-piperidin-1-yl-carboxy, 4-t.-butyloxycarbonyl-piperazin-1-yl-carboxy, 4-(4-azido-2-hydroxybenzoyl)-piperazin-1-yl-carboxy or 4-(4-azido-2-hydroxy-3-iodo-benzoyl)-piperazin-1-yl-carboxy, $R_3$ is hydrogen, ($C_{2-4}$) alkyl, carboxy, ($C_{1-4}$) alkoxycarbonyl, ($C_{1-4}$)alkylcarbamoyl, hydroxy($C_{1-4}$) alkyl, di($C_{1-4}$)alkylaminomethyl, morpholinocarbonyl or 4-(4-fluoro-benzoyl)-piperidin-1-yl-carboxy, $R_4$ is hydrogen, hydroxy, ($C_{1-4}$)alkoxy, carboxy, ($C_{2-5}$) alkanoyloxy, ($C_{1-4}$)alkoxycarbonyl, amino($C_{1-4}$) alkoxy, di($C_{1-4}$)alkylamino($C_{1-4}$)alkoxy, di($C_{1-4}$) alkylamino($C_{1-4}$)alkyl, carboxy ($C_{1-4}$)alkylcarbonyl, ($C_{1-4}$)alkoxycarbonyl($C_{1-4}$)alkoxy, hydroxy($C_{1-4}$) alkyl, di($C_{1-4}$)alkylamino($C_{1-4}$)alkoxy, m-hydroxy-p-azidophenylcarbonylamino($C_{1-4}$)alkoxy, and $R_5$ is a group of formula

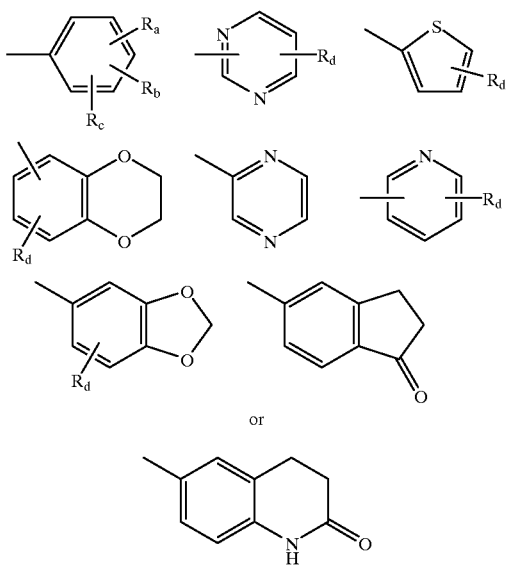

or wherein
$R_a$ and $R_b$ independently are hydrogen, hydroxy, halogen, nitro, cyano, carboxy, $(C_{1-4})$alkyl, $(C_{1-4})$alkoxy, hydroxy$(C_{1-4})$alkyl, $(C_{1-4})$alkoxycarbonyl, $(C_{2-7})$alkanoyl, $(C_{2-5})$alkanoyloxy, $(C_{2-5})$alkanoyloxy$(C_{1-4})$alkyl, trifluoromethyl, trifluoromethoxy, trimethylsilylethynyl, $(C_{2-5})$alkynyl, amino, azido, amino $(C_{1-4})$alkoxy, $(C_{2-5})$alkanoylamino$(C_{1-4})$alkoxy, $(C_{1-4})$alkylamino$(C_{1-4})$alkoxy, di$(C_{1-4})$alkylamino$(C_{1-4})$alkoxy, $(C_{1-4})$alkylamino, di$(C_{1-4})$alkylamino, monohalobenzylamino, thienylmethylamino, thienylcarbonylamino, trifluoromethylphenylaminocarbonyl, tetrazolyl, $(C_{2-5})$alkanoylamino, benzylcarbonylamino, $(C_{1-4})$alkylamino carbonylamino, $(C_{1-4})$alkoxycarbonylaminocarbonylamino or $(C_{1-4})$alkylsulfonyl, $R_c$ is hydrogen, fluorine, chlorine, bromine, hydroxy, $(C_{1-4})$alkyl, $(C_{2-5})$alkanoyloxy, $(C_{1-4})$alkoxy or cyano, and $R_d$ is hydrogen, halogen or $(C_{1-4})$alkyl, provided that in compounds wherein $R_2$, $R_3$ and $R_4$ are hydrogen, when $R_1$ is methyl, $R_5$ is different from phenyl, 3-methylphenyl, 6-methylpyridin-2-yl and 3-methoxyphenyl, in free form or in form of a pharmaceutically acceptable salt.

2. A compound of formula I according to claim 1, wherein

X represents an optionally halo-substituted $(C_{2-4})$ alkynylene group bonded via vicinal unsaturated carbon atoms, $R_1$ is $(C_{1-4})$ alkyl, $(C_{1-4})$alkoxy, cyano, ethynyl or di$(C_{1-4})$alkylamino, $R_2$ is hydrogen, hydroxy, carboxy, $(C_{1-4})$ alkoxycarbonyl, di$(C_{1-4})$alkylaminomethyl, 4-(4-fluoro-benzoyl)-piperidin-1-yl-carboxy, 4-t.-butyloxycarbonyl-piperazin-1-yl-carboxy, 4-(4-azido-2-hydroxybenzoyl)-piperazin-1-yl-carboxy or 4-(4-azido-2-hydroxy-3-iodo-benzoyl)-piperazin-1-yl-carboxy, $R_3$ is hydrogen, $(C_{1-4})$ alkyl, carboxy, $(C_{1-4})$ alkoxycarbonyl, $(C_{1-4})$alkylcarbamoyl, hydroxy$(C_{1-4})$alkyl, di$(C_{1-4})$alkylaminomethyl, morpholinocarbonyl or 4-(4-fluoro-benzoyl)-piperidin-1-yl-carboxy, $R_4$ is hydrogen, hydroxy, carboxy, $(C_{2-5})$alkanoyloxy, $(C_{1-4})$alkoxycarbonyl, amino $(C_{1-4})$alkoxy, di$(C_{1-4})$ alkylamino$(C_{1-4})$alkoxy, di$(C_{2-4})$alkylamino$(C_{1-4})$alkyl or hydroxy$(C_{1-4})$alkyl, and $R_5$ is a group of formula

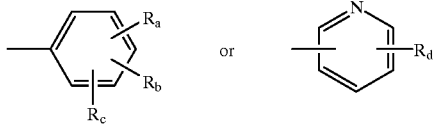

wherein
$R_a$ and $R_b$ independently are hydrogen, halogen, nitro, cyano, $(C_{1-4})$alkyl, $(C_{1-4})$alkoxy, trifluoromethyl, trifluoromethoxy or $(C_{2-5})$alkynyl, $R_c$ is hydrogen, fluorine, chlorine, bromine, hydroxy, $(C_{1-4})$alkyl, $(C_{2-5})$alkanoyloxy, $(C_{1-4})$alkoxy or cyano, and $R_d$ is hydrogen, halogen or $(C_{1-4})$alkyl, provided that in compounds wherein $R_2$, $R_3$ and $R_4$ are hydrogen, when $R_1$ is methyl, $R_5$ is different from phenyl, 3-methylphenyl, 6-methylpyridin-2-yl and 3-methoxyphenyl, in free form or in form of a pharmaceutically acceptable salt.

3. A compound according to claim 1 wherein X is ethynylene, in free form or in form of a pharmaceutically acceptable salt.

4. A compound according to claim 1 wherein $R_5$ is different from optionally substituted phenyl and X is ethynylene, in free form or in form of a pharmaceutically acceptable salt.

5. A compound according to claim 1 wherein $R_5$ is optionally substituted pyridin-3-yl and X is ethynylene, in free form or in form of a pharmaceutically acceptable salt.

6. A compound which is 2-[2-(Pyridin-3-yl)ethynyl]-6-methyl-pyridine in free form or in form of a pharmaceutically acceptable form.

7. A method of treating disorders which are mediated fully or in part by mGluR1 or mGluR5, comprising administering to a mammal in need of such treatment a therapeutically effective amount of a compound of formula I

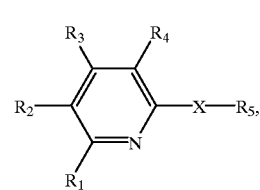

(I)

wherein
X represents an optionally halo-substituted lower alkenylene or alkynylene group bonded via vicinal unsaturated carbon atoms or an azo (—N═N—) group, $R_1$ denotes hydrogen, lower alkyl, hydroxy-lower alkyl, lower alkyl-amino, piperidino, carboxy, esterified carboxy, amidated carboxy, unsubstituted or lower alkyl-, lower alkoxy-, halo- and/or trifluoromethyl-substituted N-lower-alkyl-N-phenylcarbamoyl, lower alkoxy, halo-lower alkyl or halo-lower alkoxy, $R_2$ denotes hydrogen, lower alkyl, carboxy, esterified carboxy, amidated carboxy, hydroxy-lower alkyl, hydroxy, lower alkoxy or lower alkanoyloxy, 4-(4-fluoro-benzoyl)-piperidin-1-yl-carboxy, 4-t.-butyloxycarbonyl-piperazin-1-yl-carboxy, 4-(4-azido-2-hydroxybenzoyl)-piperazin-1-yl-carboxy or 4-(4-azido-2-hydroxy-3-iodo-benzoyl)-piperazin-1-yl-carboxy, $R_3$ represents hydrogen, lower alkyl, carboxy, lower alkoxy-carbonyl, lower alkyl-carbamoyl, hydroxy-lower alkyl, di-lower alkyl-aminomethyl, morpholinocarbonyl or 4-(4-fluoro-benzoyl)-piperidin-1-yl-carboxy, $R_4$ represents hydrogen, lower alkyl, hydroxy, hydroxy-lower alkyl, amino-lower alkyl, lower alkylamino-lower alkyl, di-lower alkylamino-lower alkyl, unsubstituted or hydroxy-substituted lower alkyleneamino-lower alkyl, lower alkoxy, lower alkanoyloxy, amino-lower alkoxy, lower alkylamino-lower alkoxy, di-lower alkylamino-lower alkoxy, phthalimido-lower alkoxy, unsubstituted or hydroxy- or 2-oxo-imidazolidin-1-yl-substituted lower alkyleneamino-lower alkoxy, carboxy, esterified or amidated carboxy, carboxy-lower-alkoxy or esterified carboxy-lower-alkoxy, and $R_5$ denotes an aromatic or heteroaromatic group which is unsubstituted or substituted by one or more substituents selected from lower alkyl, halo, halo-lower alkyl, halo-lower alkoxy, lower alkenyl, lower alkynyl, unsubstituted or lower alkyl-, lower alkoxy-, halo- and/or trifluoromethyl-substituted phenyl, unsubstituted or lower alkyl-, lower alkoxy-, halo- and/or trifluoromethyl-substituted phenyl-lower alkynyl, hydroxy, hydroxy-lower alkyl, lower alkanoyloxy-lower alkyl, lower alkoxy, lower alkenyloxy, lower alkylenedioxy, lower alkanoyloxy, amino-, lower alkylamino-, lower alkanoylamino- or N-lower alkyl-N-lower alkanoylamino-lower alkoxy, unsubstituted or lower alkyl-lower alkoxy-, halo- and/or trifluoromethyl-substituted phenoxy, unsubstituted or lower alkyl-lower alkoxy-, halo- and/or trifluoromethyl-substituted phenyl-lower alkoxy, acyl, carboxy, esterified carboxy, amidated carboxy, cyano, carboxy-lower alkylamino, esterified carboxy-lower alkylamino, amidated carboxy-lower alkylamino, phosphono-lower alkylamino, esterified phosphono-lower alkylamino, nitro, amino, lower alkylamino, di-lower alkylamino, acylamino, N-acyl-N-lower alkylamino, phenylamino, phenyl-lower alkylamino, cycloalkyl-lower alkylamino or heteroaryl-lower alkylamino each of which may be unsubstituted or lower alkyl-lower alkoxy-, halo- and/or trifluoromethyl-substituted, in free form or in the form of a photoaffinity ligand, a radioactive marker, an N-oxide or a pharmaceutically acceptable salt.

8. A pharmaceutical composition comprising a pharmaceutically acceptable carrier or diluent and a therapeutically effective amount of a compound according to claim 1, in free form or in the form of a pharmaceutically acceptable salt.

\* \* \* \* \*

UNITED STATES PATENT AND TRADEMARK OFFICE
CERTIFICATE OF CORRECTION

PATENT NO. : 6,656,957 B1
DATED : December 2, 2003
INVENTOR(S) : Allgeier et al.

It is certified that error appears in the above-identified patent and that said Letters Patent is hereby corrected as shown below:

Title page,
Item [*] Notice, delete the phrase "by 0 days" and insert -- by 567 days --

Signed and Sealed this

Twentieth Day of July, 2004

JON W. DUDAS
*Acting Director of the United States Patent and Trademark Office*